(12) United States Patent
Pasternak et al.

(10) Patent No.: US 9,341,551 B2
(45) Date of Patent: May 17, 2016

(54) DEVICE AND METHOD FOR HANDLING BIOLOGICAL TISSUES

(71) Applicant: UC-CARE LTD., Yokneam (IL)

(72) Inventors: Alex Pasternak, Tel Aviv (IL); Keren Shapira-Schweizer, Tal El (IL); Shaike Schatzberger, Haifa (IL)

(73) Assignee: UC-CARE LTD., Yokneam (IL)

( * ) Notice: Subject to any disclaimer, the term of this patent is extended or adjusted under 35 U.S.C. 154(b) by 15 days.

(21) Appl. No.: 14/370,645

(22) PCT Filed: Jan. 10, 2013

(86) PCT No.: PCT/IL2013/050031
§ 371 (c)(1),
(2) Date: Jul. 3, 2014

(87) PCT Pub. No.: WO2013/105095
PCT Pub. Date: Jul. 18, 2013

(65) Prior Publication Data
US 2014/0377148 A1    Dec. 25, 2014

Related U.S. Application Data

(60) Provisional application No. 61/584,833, filed on Jan. 10, 2012, provisional application No. 61/590,932, filed on Jan. 26, 2012, provisional application No. 61/694,270, filed on Aug. 29, 2012, provisional application No. 61/706,042, filed on Sep. 26, 2012.

(51) Int. Cl.
*B01L 9/00*     (2006.01)
*G01N 1/31*     (2006.01)
(Continued)

(52) U.S. Cl.
CPC ............ *G01N 1/312* (2013.01); *A61B 10/0096* (2013.01); *A61B 10/0266* (2013.01); *A61B 10/0275* (2013.01); *B01L 9/52* (2013.01); *G01N 1/2813* (2013.01); *G01N 1/36* (2013.01); *G01N 2001/2833* (2013.01)

(58) Field of Classification Search
CPC .... A61B 10/0096; B01L 9/52; G01N 1/2813; G01N 1/312; G01N 1/36; G01N 2001/2833
See application file for complete search history.

(56) References Cited

U.S. PATENT DOCUMENTS 2,732,581 A    1/1956    Heck
4,738,664 A    4/1988    Prindle
(Continued)

FOREIGN PATENT DOCUMENTS

EP    1932480    6/2008
JP    2004-028985    1/2004
(Continued)

OTHER PUBLICATIONS

Ficarra et al., (2006) Needle core length is a quality indicator of systematic transperineal prostate biopsy. Eur Urol 50 (2): 266-71.

*Primary Examiner* — Paul Hyun
(74) *Attorney, Agent, or Firm* — Rodney J. Fuller; Booth Udall Fuller, PLC

(57) ABSTRACT

A tissue handling device is disclosed. A tissue collecting device is disclosed. A cassette for handling biological tissues is disclosed. A tissue dyeing device is disclosed. A method for handling biological tissues is disclosed. A method for dyeing biological tissues is disclosed.

7 Claims, 26 Drawing Sheets

(51) Int. Cl.
*A61B 10/02* (2006.01)
*A61B 10/00* (2006.01)
*G01N 1/28* (2006.01)
*G01N 1/36* (2006.01)

(56) References Cited

U.S. PATENT DOCUMENTS

| | | |
|---|---|---|
| 4,929,426 A | 5/1990 | Bodai |
| 5,526,822 A | 6/1996 | Burbank |
| 5,612,218 A | 3/1997 | Busch |
| 5,817,032 A | 10/1998 | Williamson, IV |
| 6,364,866 B1 | 4/2002 | Furr |
| 6,395,234 B1 | 5/2002 | Hunnell |
| 6,458,410 B1 | 10/2002 | Ikami |
| 6,719,691 B2 | 4/2004 | Kritzman |
| 7,156,814 B1 | 1/2007 | Williamson, IV |
| 7,179,424 B2 | 2/2007 | Williamson, IV |
| 7,445,603 B2 | 11/2008 | Zimmon |
| 7,776,274 B2 | 8/2010 | Williamson, IV |
| 7,794,411 B2 | 9/2010 | Ritchart |
| 8,052,615 B2 | 11/2011 | Reuber |
| 8,071,058 B2 | 12/2011 | Haywood |
| 2004/0030263 A1 | 2/2004 | Dubrul |
| 2004/0043481 A1 | 3/2004 | Wilson |
| 2005/0112034 A1 | 5/2005 | McCormick |
| 2005/0211588 A1 | 9/2005 | Kanner |
| 2007/0116612 A1* | 5/2007 | Williamson, IV .. A61B 10/0096 422/400 |
| 2008/0287826 A1 | 11/2008 | Videbaek |
| 2009/0050516 A1 | 2/2009 | Hardin |
| 2010/0075410 A1 | 3/2010 | Desai |
| 2010/0106055 A1 | 4/2010 | Heske |
| 2010/0160816 A1 | 6/2010 | Parihar |
| 2010/0160824 A1 | 6/2010 | Parihar |
| 2010/0184127 A1 | 7/2010 | Williamson, IV |
| 2010/0330659 A1 | 12/2010 | Poulsen |
| 2011/0034758 A1 | 2/2011 | Shany |
| 2011/0054350 A1 | 3/2011 | Videbaek |
| 2011/0086378 A1 | 4/2011 | Shany |
| 2011/0281297 A1 | 11/2011 | Chekan |
| 2011/0282239 A1 | 11/2011 | Conlon |

FOREIGN PATENT DOCUMENTS

| | | |
|---|---|---|
| JP | 2005-199044 | 7/2005 |
| JP | 2009-014355 | 1/2009 |
| JP | 2009-532081 | 9/2009 |
| WO | 2007/039905 | 4/2007 |
| WO | 2007/112751 | 10/2007 |
| WO | 2009/074154 | 6/2009 |
| WO | 2010/071748 | 6/2010 |
| WO | 2010/080298 | 7/2010 |
| WO | 2011/161684 | 12/2011 |

* cited by examiner

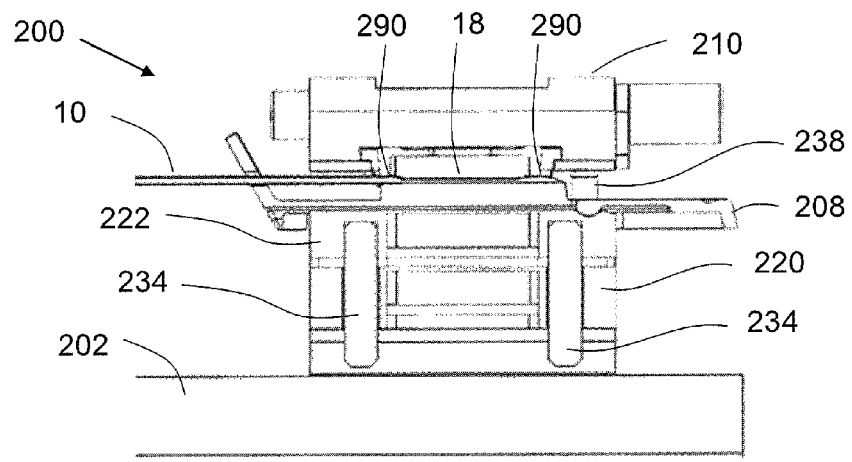
Figure 12
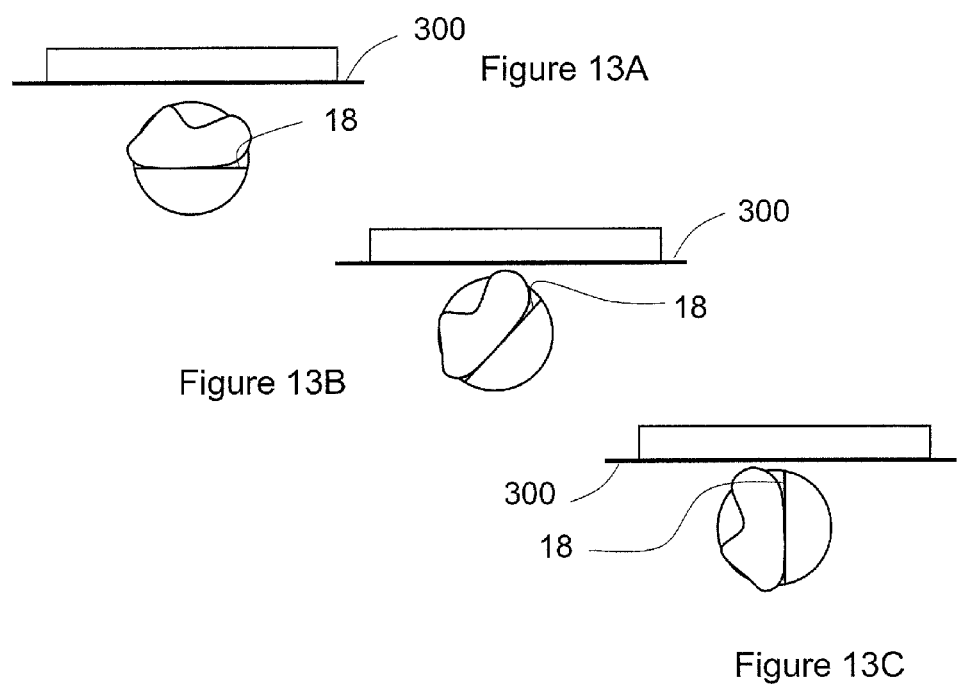
Figure 13A
Figure 13B
Figure 13C

DEVICE AND METHOD FOR HANDLING BIOLOGICAL TISSUES

CROSS-REFERENCE TO RELATED APPLICATIONS

This patent application is the U.S. National Stage of International Application No. PCT/IL2013/050031, filed Jan. 10, 2013, which claims the benefit of U.S. Provisional Application No. 61/584,833, filed Jan. 10, 2012; U.S. Provisional Application No. 61/590,932, filed Jan. 26, 2012; U.S. Provisional Application No. 61/694,270, filed Aug. 29, 2012; and U.S. Provisional Application No. 61/706,042, filed Sep. 26, 2012; each of which are herein incorporated by reference thereto in their entireties for all purposes.

FIELD OF THE INVENTION

The invention, in some embodiments, relates to the field of handling biological tissues, and more particularly, but not exclusively, to devices and methods intended for handling biological tissues that are taken with a biopsy needle.

BACKGROUND OF THE INVENTION

Core biopsy is a routine procedure used to obtain a sample of a biological tissue from a live organ for a laboratory examination. FIGS. 1A-1D depict schematically a core biopsy needle 10 used for taking core biopsy samples. Core biopsy needle 10 comprises a mandrel 12 and a Cannula 14. Mandrel 12 is an elongated solid needle having a distal tip 16 at the end of needle 10 and a notch 18 adjacent to distal tip 16. Notch 18 is an interior shaft recess, used for receiving the tissue sample. Cannula 14 is a sleeve exterior to mandrel 12 and is configured for sliding over mandrel 12.

During a core biopsy procedure distal tip 16 of core biopsy needle 10 is brought up to a few millimeters from a region to be sampled in an organ (FIG. 1A). Mandrel 12 is advanced forward into the organ, typically at a high speed to reduce pain in an awakened patient, allowing organ tissue to fill in notch 18 (FIG. 1B). Cannula 14 is then advanced forward over the mandrel, thereby cutting off a sample tissue which is left in notch 18 (FIG. 1C). Core biopsy needle 10 is removed from the organ and Cannula 14 is pulled back in order to expose and remove the sample tissue from notch 18 (FIG. 1D). The sample tissue is typically removed from notch 18 into a vial filled with a preservative solution such as a solution including formaldehyde, usually by hand using a syringe or using a small sharp-end tool. Several sample tissues may be put in a single vial during such a core biopsy procedure, being left in the preservative solution until taken through a preparation process for laboratory examination.

A typical preparation process prior to examination is detailed for example in U.S. Pat. No. 7,156,814, and may include the following steps:

a. A sample is manually taken out of the preservative solution using an appropriate tool, and placed in a sample box. Inside the sample box the sample is gently pressed, using a box cover, between two sheets of a soft material such as a sponge, which prevents displacement of the sample tissue inside the box. An example of a sample box is Tissue-Tek® Uni-Cassettes® by SAKURA FINETEK USA, INC. The sample box is then marked with a string (e.g. digits and letters) identifying the sample and its origin.

b. The tissue inside the box is taken through a chemical process of several hours, involving immersion in neutral buffered formaldehyde preservative solution, in ethanol, in xylene and in paraffin. Then the sample tissue is dried.

c. Dried tissue is removed from the sample box and placed in a metal mold, about the size of the sample box. The sample tissue is fixed to the base of the mold, typically using a drop of paraffin and by gently pressing onto the sample tissue. An example of a metal mold is Tissue-Tek® Base Molds by SAKURA FINETEK USA, INC.

d. The sample box, without cover, is fixed on top of the metal mold, and the space within, that is to say between the metal mold and the sample box, is filled with paraffin.

e. After the paraffin solidifies the metal mold is removed, leaving the sample box (with the marked string identifying the sample tissue) filled with a block of paraffin and with the sample tissue on top.

f. The sample box with the sample tissue is taken for slicing. Slices of typical thickness of a few microns are taken from the top surface of the paraffin block, carrying slices of the sample tissue therein.

g. A selected slice is placed between two glass plates and inserted to an oven for melting the paraffin. After removing the liquid paraffin, the sample tissue between two glass plates is taken for examination, e.g. under a microscope.

SUMMARY OF THE INVENTION

In recent years there is continuous trend towards more localized diagnose for many diseases, e.g. local diagnose of prostate cancer. A more localized diagnose enables a more localized treatment, leading to reducing healing time and collateral damage during and after treatment, increasing healing likelihood, decreasing patient suffer and inconvenience and reducing overall treatment cost. Local diagnose procedures rely on the ability to gather accurate data regarding not only the disease histological characteristics but specifically the spatial location of the disease within the organ. Specifically, recent developments in the field of imaging and tracking techniques of treatment tools have led to improved ability of tracing a treatment tool, for example a biopsy needle, within the body. Devices and methods for increasing positioning accuracy of a medical instrument and recording positioning measurements during a medical procedure—e.g. core biopsy—are described for example in PCT patent publications WO/2007039905 and WO/2011161684.

However, the current biopsy needles and tissue handling techniques are inherently limited by the shortage of devices and methods that may deliver the required spatial resolution, tissue harvesting efficiency and adequacy of post-biopsy tissue handling, for optimized histological review. Commonly, in the course of a diagnostic procedure involving obtaining core biopsy samples, several samples are taken from several locations in the inspected organ. For example, when core biopsy samples are taken from a prostate to confirm or refute a suspicion of prostate cancer, about six samples, typically, are taken from each half (left and right) of the prostate. The surgeon attempts to distribute the locations from where the samples are taken over the volume of each half, so as to decrease interdependency between samples and thereby increase detection likelihood. However, with current samples handling procedures, several samples, and often all six samples from one half of the prostate, are inserted into a same vial immediately after taking. As a result, all information about the original location from where a particular sample was taken in the prostate is lost. It is only known that the samples in a certain vial were taken from a particular half (left or right) of the prostate.

Yet, even employing an ideal procedure with currently available devices and tools would still be deficient. Such an ideal procedure may comprise, for example, (1) a perfectly accurate spatial tracing of the biopsy needle while taking a core biopsy sample in the organ, (2) inserting each single sample to a separate vial, and (3) identifying on each such vial the sample that is inside, for example by marking a serial number of the sample on the vial, thereby allowing to correlate later on each sample with the location from where the sample was taken. Yet, with the current needles and tissue handling techniques, even such an ideal procedure may lead to a spatial location uncertainty of more than 20 mm. This spatial uncertainty corresponds to the core axis and is as large as the notch length.

When the biopsy needle axis is referred to as the Z axis and the perpendicular plane as the X-Y plane, it is noted that X or Y axis location estimation errors are only those of the needle spatial recognition through, e.g., an imaging modality and/or a tracking modality. It is assumed that tracing and imaging techniques are able to provide an error of no more than a few millimeters, and possibly less than one millimeter, in the X-Y plane. By using some imaging and tracking techniques, similar accuracy of a few millimeters or even less than one millimeter may be achieved for the location of the needle Distal tip. However, Z-axis inaccuracy of the sample original location is dominated not by the needle spatial recognition available through such techniques, but rather by inherent uncertainty resulting from the available biopsy needles designs and the tissue core handling as is explained below.

As tissue cores are usually inserted into vials containing preservative solutions, the original orientation of the core sample within the organ is lost, leading to a Z axis inaccuracy of 20 mm or more, depending on the needle notch length. Free floating cores may break into smaller pieces, of which original orientation is unknown, leading again to a Z axis inaccuracy of 20 mm or more, depending on the core length. Moreover, such breaking of core samples often results in loss of pieces of a sample/specimen, resulting in turn in substantial reduction of detection probability. Further, an average tissue core length can occasionally be only 50-60% of its full potential length (i.e. the length of the needle notch). This also results in an average Z axis inaccuracy of 10 mm for a 20 mm notch length. Further, fixation of a tissue core in preservative solution results in shrinkage that, depending on the tissue type and size as well as other variables, may decrease some 30% of the specimen original size.

Herein the terms "notch" and "notch floor" are used interchangeably, referring to the shaft on which a sample tissue is supported, as well as to the volume taken by the sample above the notch floor. Thus, a sample may be referred to as being supported "in" the notch, or supported "on" the notch, or supported "on the notch floor", and so on. Accordingly, "the notch faces direction A" should be interpreted as meaning "the notch floor faces direction A", whereas the direction the notch floor faces is the direction of the normal to the notch floor.

Herein are provided devices and methods that in some aspects improve techniques for collecting onto a sample holder a biological tissue carried on a shaft. In some embodiments, collecting a biological tissue from a shaft onto a sample holder reduces damage to the biological tissue, retains the tissue's integrity and preserves the tissue's orientation. Specifically, devices and methods are provided that in some aspects improve techniques for handling biological tissues that are taken with a biopsy needle. Devices and methods are provided herein that in some embodiments maintain sample tissue orientation and/or allow Z axis inaccuracy of not more than 1 millimeter and even Z axis accuracy better than 1 millimeter. Devices and methods are provided that in some embodiments enable increased disease detection probability.

Thus, according to an aspect of some embodiments, there is provided a device for handling core biopsy tissues taken using a core biopsy needle having a notch. The device comprises a base, a lever and a needle bed physically associated with one of the base and the lever, and configured to support a core biopsy needle substantially in a pre-defined position. The other of the base and the lever is configured to attach to a sample holder so that the sample holder may be facing a core biopsy needle supported by the needle bed. The lever is physically associated with the base and is movable between settings relative the base. Thus, a sample holder attached to the device and a core biopsy needle, supported by the needle bed, are movable relative to one another. In a first setting of the lever relative to the base the sample holder may touch a core biopsy tissue initially attached to the notch of the core biopsy needle, thereby attaching the core biopsy tissue to the sample holder. In a second setting of the lever relative to the base, the sample holder and the notch of the biopsy needle are distant from one another.

In some embodiments the needle bed is physically associated with the base and the lever is configured to attach to a sample holder. In some embodiments the needle bed is physically associated with the lever and the base is configured to attach to a sample holder.

In some embodiments the lever is physically associated with the base by a pivot, thereby being movable between settings relative to the base substantially along an arc. In some embodiments the lever is physically associated with the base by a track, thereby being movable between settings relative to the base substantially along a linear trajectory. In some embodiments the track comprises rails. In some embodiments the track comprises grooves.

In some embodiments the notch of the core biopsy needle may comprise a notch floor and the sample holder is configured to touch the core biopsy tissue from a direction substantially across from the notch floor, thereby pressing the core biopsy tissue between the sample holder and the notch floor. In some embodiments the sample holder is configured to touch the core biopsy tissue from a direction substantially not across from the notch floor, thereby not pressing the core biopsy tissue between the sample holder and the notch floor.

In some embodiments the sample holder comprises a sample sheet, capable of adhering to a core biopsy tissue by touching the core biopsy tissue.

In some embodiments the sample holder comprises a cassette. In some embodiments the cassette is configured to hold a sample sheet, capable of adhering to a core biopsy tissue by touching the core biopsy tissue.

In some embodiments the core biopsy tissue is attached to the sample holder so that an orientation of the core biopsy tissue on the notch is substantially maintained on the sample holder.

In some embodiments the device further comprises a dying module configured for selectively colouring a core biopsy sample in a portion thereof by touching the portion. In some embodiments the sample holder may touch the dying module in a setting of the lever relative to the base, so that a core biopsy tissue attached to the sample holder is selectively coloured in a portion thereof that is associated with a pre-defined portion of the notch of the biopsy needle.

Aspects and embodiments of the invention are further described in the specification herein below.

Unless otherwise defined, all technical and scientific terms used herein have the same meaning as commonly understood by one of ordinary skill in the art to which this invention pertains. In case of conflict, the patent specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, the terms "sample tissue", "sample" and "specimen" may be used interchangeably.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 12 schematically depicts a cross section of the pedestal and the lever of the tissue handling device of FIG. 7A in closed position with a biopsy needle;

FIG. 13A schematically depicts a cross-section view of an embodiment of a sample holder and a biopsy needle secured in a tissue handling device, wherein the notch has a parallel orientation relative to the sample holder;

FIG. 13B schematically depicts a cross-section view of an embodiment of a sample holder and a biopsy needle secured in a tissue handling device, wherein the notch has a tilted orientation relative to the sample holder;

FIG. 13C schematically depicts a cross-section view of an embodiment of a sample holder and a biopsy needle secured in a tissue handling device, wherein the notch has a perpendicular orientation relative to the sample holder;

DESCRIPTION OF SOME EMBODIMENTS OF THE INVENTION

Figure 1A:
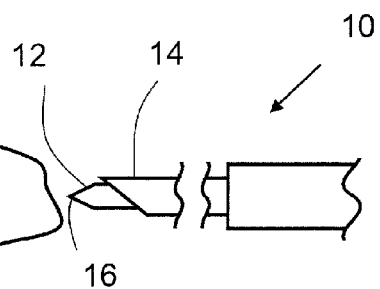
FIG. 1A (prior art) schematically depicts a core biopsy needle prior to obtaining a sample from an organ.
Figure 1B:
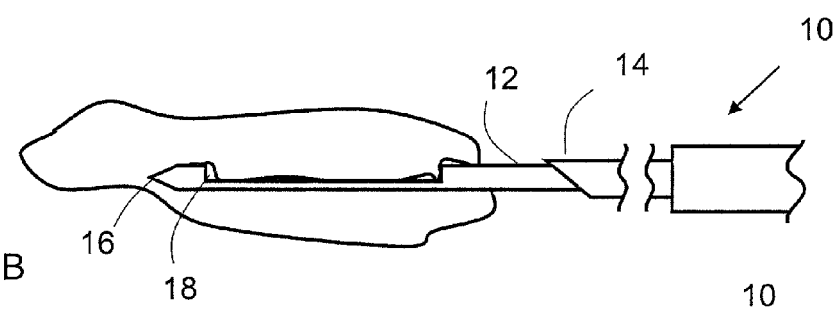
FIG. 1B (prior art) schematically depicts a core biopsy needle when the mandrel is advanced into the organ and organ tissue fills the notch.
Figure 1C:
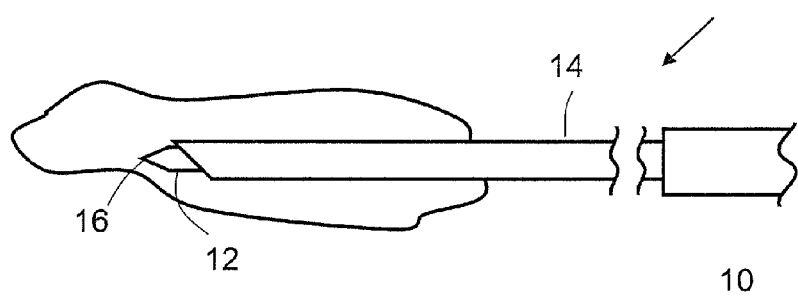
FIG. 1C (prior art) schematically depicts a core biopsy needle when the cannula is advanced over the mandrel.
Figure 1D:
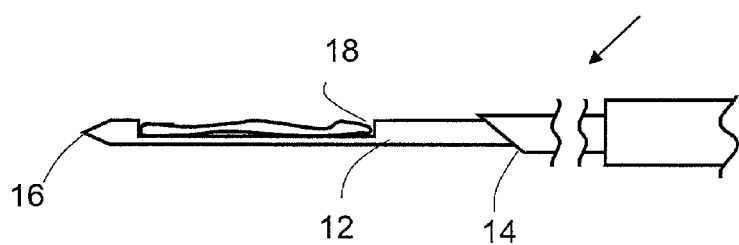
FIG. 1D (prior art) schematically depicts a core biopsy needle when the cannula is pulled back to expose a sample tissue on the notch.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Figure 2A:
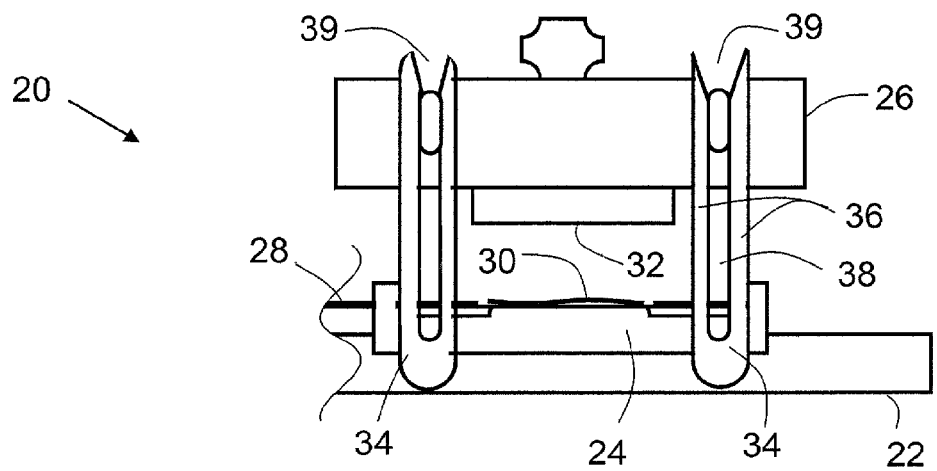
FIG. 2A schematically depicts an embodiment of a tissue collecting device comprising a base and a lever, a needle bed attached to the base and a sample holder attached to the lever.

An embodiment of a tissue collecting device 20 as described herein is schematically depicted in FIG. 2A. Tissue collecting device 20 comprises a base 22, a needle bed 24 attached to base 22 and a lever 26. Needle bed 24 is configured to support, substantially in a pre-defined position, a shaft 28 carrying a biological tissue 30. A sample holder 32 is attached to lever 26, substantially facing needle bed 24. For use, shaft 28 is supported by needle bed 24 in a pre-defined position, thus having a substantially unique location and orientation relative to needle bed 24 and to base 22. Further, shaft 28 is supported by needle bed 24 so that tissue 30 on shaft 28 faces sample holder 32.

Tracks 34 are fixedly attached to base 22, each comprising a pair of rails 36 and a groove 38 between the rails. Lever 26 is movable, substantially up and down along tracks 34, between several settings. In a first setting schematically depicted in FIG. 2A, lever 26 is distant from needle bed 24. Lever 26 may be moved down to a second setting (not shown), so that sample holder 32 is proximal to needle bed 24, having a pre-defined arrangement relative to needle bed 24. Tracks 34 confine movement of lever 26, so that lever 26 may move substantially only up and down (e.g. between the first setting and the second setting), whereas sample holder 32 is maintained substantially parallel to needle bed 24. When shaft 28, carrying biological tissue 30 thereon, is suitably supported on needle bed 24, sample holder 32 is also substantially parallel to shaft 28, and sample holder 32 may touch biological tissue 30 when lever 26 is in the second setting. According to some embodiments, sample holder 32 may adhere to biological tissue 30 by touching. According to some embodiments sample holder 32 may adhere to biological tissue 30 by pressing. According to some embodiments, sample holder 32 may adhere to biological tissue 30 when lever 26 is in the second setting, and may further detach biological tissue 30 from shaft 28 when moved up to the first setting. Lever 26 is further detachable from base 22 and may be detached from base 22 by moving lever 26 up beyond the first setting and through openings 39 until lever 26 is not confined by tracks 34.

Figure 2B:
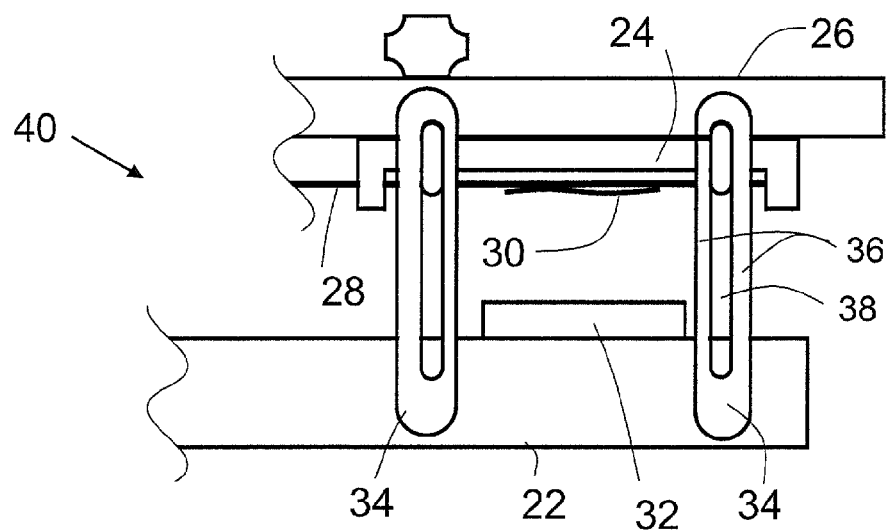
FIG. 2B schematically depicts an embodiment of a tissue collecting device comprising a base and a lever, a needle bed attached to the lever and a sample holder attached to the base.

A further embodiment of a tissue collecting device 40 as described herein is schematically depicted in FIG. 2B. Tissue collecting device 40 has similar functionality as tissue collecting device 20, comprising lever 26 movable substantially up and down along tracks 34, between settings, relative to base 22. Tissue collecting device 40 is different from tissue collecting device 20 in that needle bed 24 is attached to lever 26 rather than being attached to base 22, whereas base 22 is configured to support sample holder 32 attached thereto. Shaft 28 may be positioned in place and supported by needle bed 24 in a pre-defined position facing sample holder 32, thereby being movable relative to sample holder 32 together with lever 26. In a first setting, depicted schematically in FIG. 2B, lever 26 is distant from base 22 thereby needle bed 24 is distant from sample holder 32. Lever 26 is may be moved down to a second setting (not shown) so that needle bed 24 is proximal to sample holder 32, having a pre-defined arrangement relative to sample holder 32. Tracks 34 confine movement of lever 26, so that lever 26 may move substantially only up and down (e.g. between the first setting and the second setting), whereas needle bed 24 is maintained substantially parallel to sample holder 32. When shaft 28, carrying biological tissue 30 thereon, is suitably supported by needle bed 24, shaft 28 is also substantially parallel to sample holder 32, and biological tissue 30 may touch sample holder 32, and thereby adhere to sample holder 32, when lever 26 is in the second setting.

An embodiment of a tissue handling device 50 as described herein is schematically depicted in FIGS. 3A-3F. According to some embodiments, tissue handling device 50 is configured for collecting biopsy samples from a biopsy needle onto a sample sheet held by a cassette. Simple handling of biopsy samples (e.g. moving a sample from place to place, inserting a sample into a container or removing a sample from a container, and so on) is then enabled or at least facilitated by handling the sample sheet carrying the core biopsy sample or by handling the cassette.

Figure 3A:
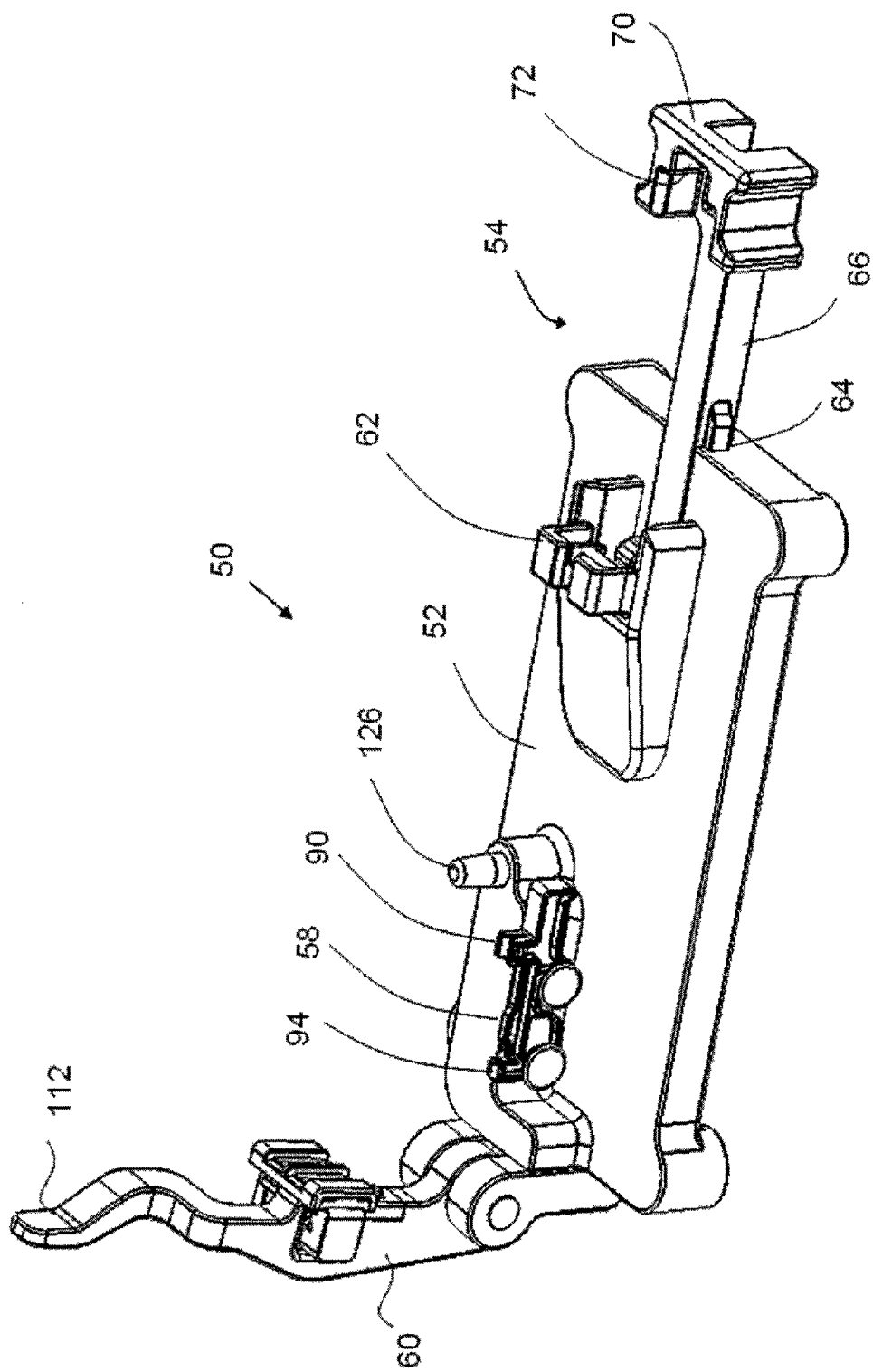
FIG. 3A schematically depicts an embodiment of a tissue handling device in perspective.
Figure 3B:
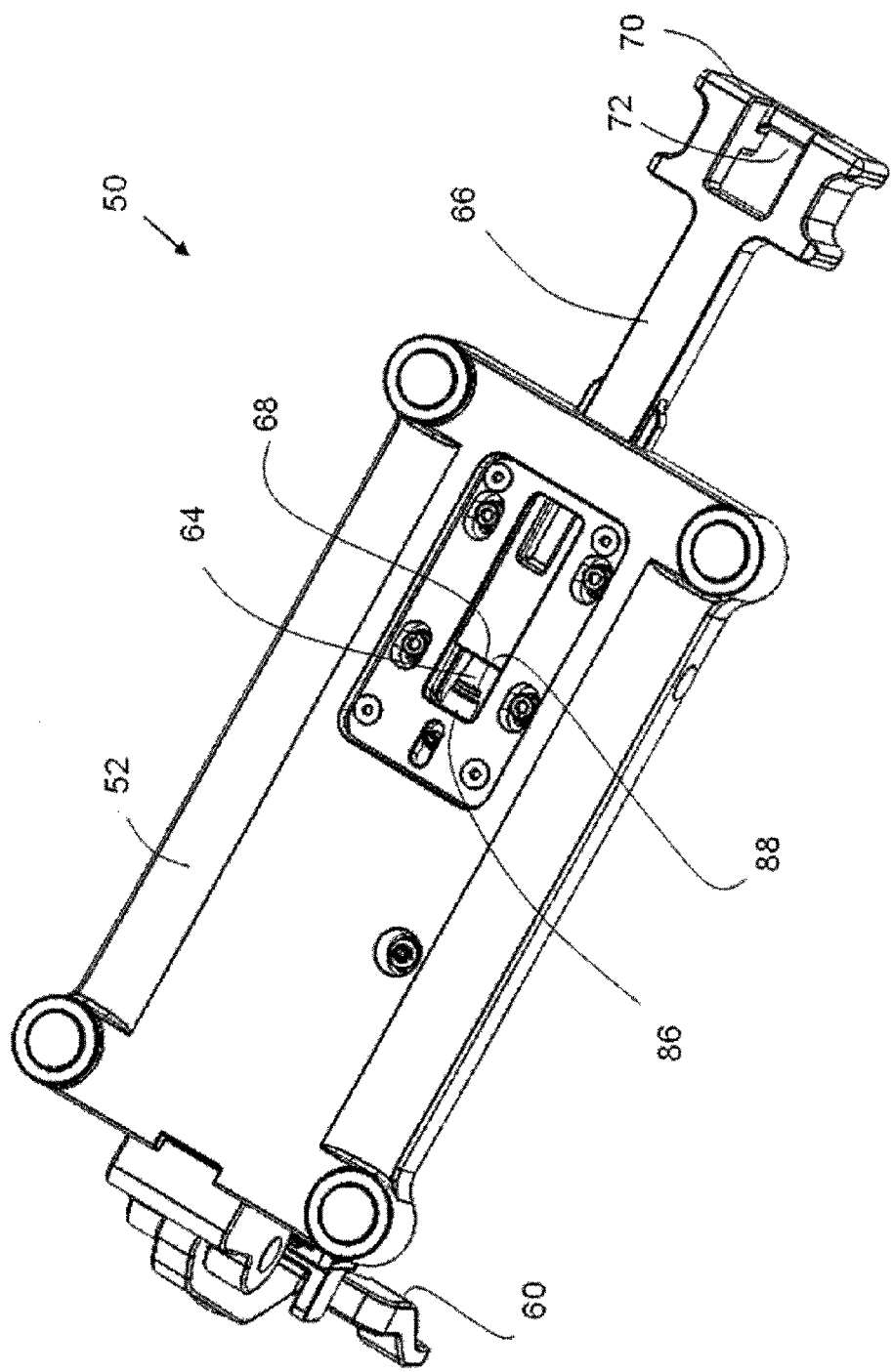
FIG. 3B schematically depicts the tissue handling device of FIG. 3A from a bottom view, in perspective.
Figure 3C:
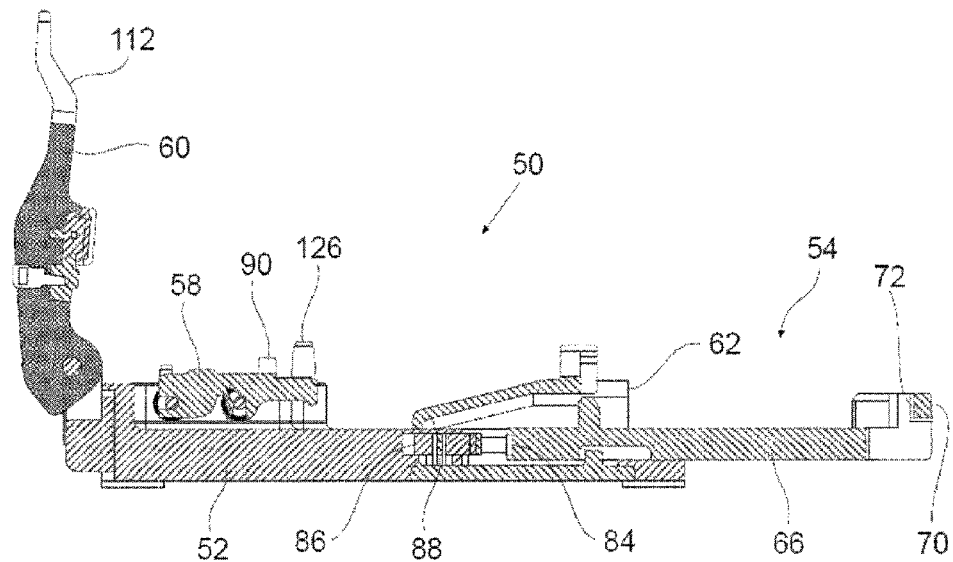
FIG. 3C schematically depicts a cross section of the tissue handling device of FIG. 3A.
Figure 3D:
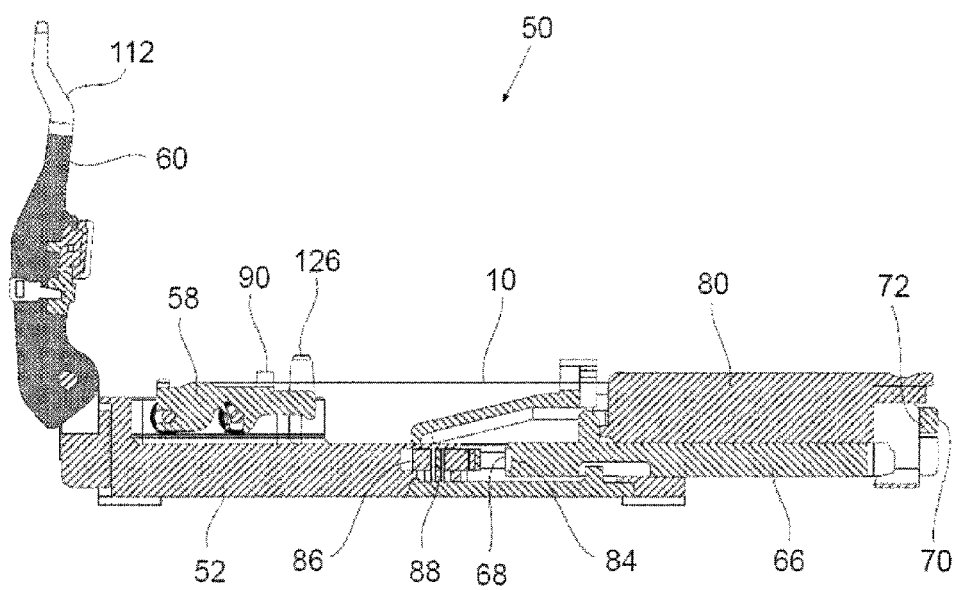
FIG. 3D schematically depicts a cross section of the tissue handling device of FIG. 3A, with an embodiment of a biopsy gun in the gun house.
Figure 3E:
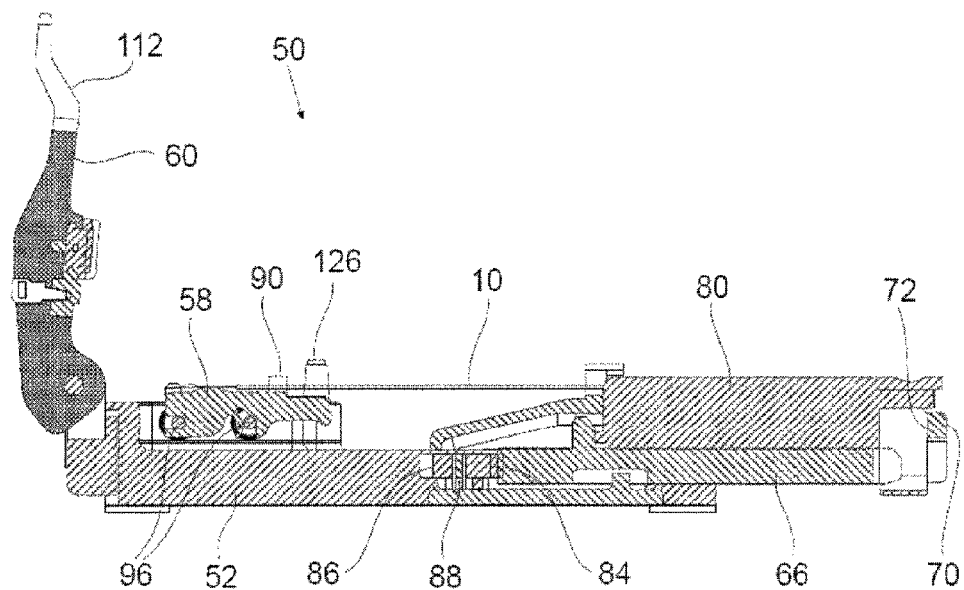
FIG. 3E schematically depicts a cross section of the tissue handling device of FIG. 3A, with an embodiment of a biopsy gun secured in the gun house.

Tissue handling device 50 comprises a base 52, a gun house 54, a needle bed 58 and a lever 60. Base 52 comprises a front stopper 62, a sliding groove 64 and a sliding table 66, having a front end 68 (FIG. 3B), a back end 70 and a back stopper 72 proximal to back end 70. Gun house 54 is configured to secure in a pre-defined position a biopsy gun 78, having a gun handle 80 and a biopsy needle 10, as is schematically depicted in FIGS. 3C-3E. The gun house is substantially formed between the front stopper 62 and the back stopper 72. The sliding table is configured to slide back and forth inside the sliding groove of the base. When the sliding table is pulled backwards so as to increase the distance between the front stopper and the back stopper, gun house 54 is opened for receiving therein a gun handle 80, as is depicted schematically in FIGS. 3D and 3E. The gun house is configured for securing in a pre-defined position, a biopsy gun, by pushing the sliding table forward, so as to decrease the distance between the front stopper and the back stopper, until back stopper 72 presses onto handle 80 of biopsy gun 78.

Reference is now drawn to FIGS. 3C-3E, schematically depicting a cross-section of tissue handling device 50 in side view, with gun house 54 open and empty (FIG. 3C), with gun house open and comprising gun handle 80 therein (FIG. 3D), and with gun house 54 closed, securing gun handle 80 and biopsy gun 78 (FIG. 3E). Sliding table 66 further comprises a table magnet 84, secured on front end 68 of the sliding table. Base 52 further comprises a locking member 86, comprising a locking magnet 88. Locking member is adjustably positioned proximal to or substantially inside sliding groove 64 in base 52. When sliding table 66 is pushed forward, thereby securing a biopsy gun inside gun house 54, table magnet 84 reaches proximal to locking magnet 88. Magnetic attraction between locking magnet 88 and table magnet 84 generates a force on sliding table 66 in a forward direction, causing sliding table 66 to press gently on the biopsy gun and secure the biopsy gun inside gun house 54. When a biopsy gun is secured inside gun house 54, front stopper 62 and back stopper 72 prevent substantial displacements of the biopsy gun sideways, forward and backwards, whereas biopsy needle 10 may thereby be positioned in place, supported by needle bed 58.

Figure 3F:
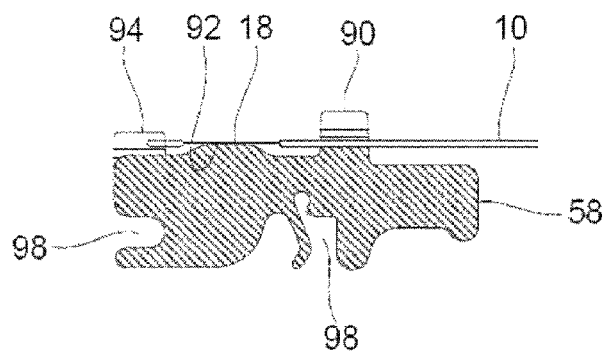
FIG. 3F schematically depicts an embodiment of a biopsy needle on the needle bed of the tissue handling device of FIG. 3A.

Needle bed 58 is depicted schematically in FIG. 3F. Needle bed 58 comprises two alignment shoulders 90 on top of a support surface 92. Needle bed 58 further comprises a positioning sleeve 94, aligned horizontally on top of support surface 92. Needle bed 58 may be substantially exposed to body fluids due to contact with biopsy needle 10, and therefore needs to be replaced after a last sample tissue is taken from the live organ in a biopsy session. Needle bed 58 is attached to base 52 by pins 96 on base 52 and slits 98 in needle bed 58 and can be detached from the base and attached to the base quickly by hand.

When it is desired to secure a biopsy gun in the gun house, sliding table 66 is pulled fully backwards so as to allow the handle of the biopsy gun to enter the gun house between front stopper 62 and back stopper 72 and leaving a space between the gun handle and the front stopper as is depicted schematically in FIG. 3D. The biopsy gun is placed on the sliding table, attached to the back stopper thereby being displaced backwards from the front stopper. Biopsy needle 10 is aligned between shoulders 90 of needle bed 58 so that the biopsy needle is aligned horizontally, in line with the symmetry axis of positioning sleeve 94 and the distal tip of the biopsy needle is outside the positioning sleeve.

For securing the biopsy gun in place, the sliding table is pushed forward, thereby pushing the biopsy gun so that biopsy needle 10 enters the positioning sleeve as is depicted schematically in FIG. 3E. When the handle of the biopsy gun contacts the front stopper, no further displacement forward is possible and biopsy needle 10 is thus secured in its pre-defined position. Magnetic attraction between locking magnet 88 and table magnet 84 generates a force on sliding table 66 forward, thereby securing the biopsy gun in place.

Figure 4A:
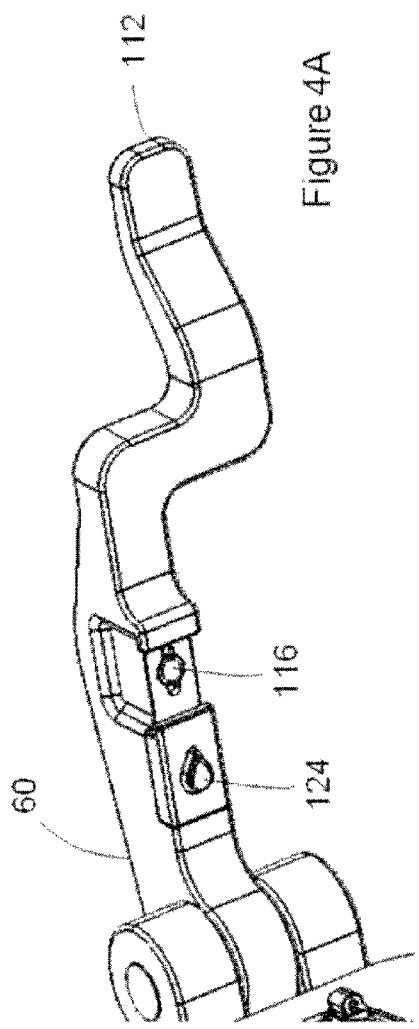
FIG. 4A schematically depicts the lever of the tissue handling device of FIG. 3A in perspective view.
Figure 4C:
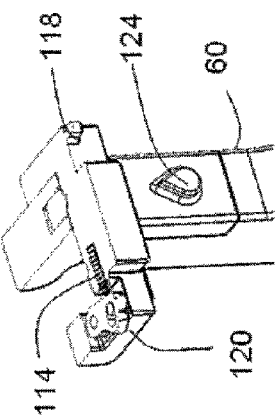
FIG. 4C schematically depicts a cross section of the cassette holder of FIG. 4B in perspective view.
Figure 4B:
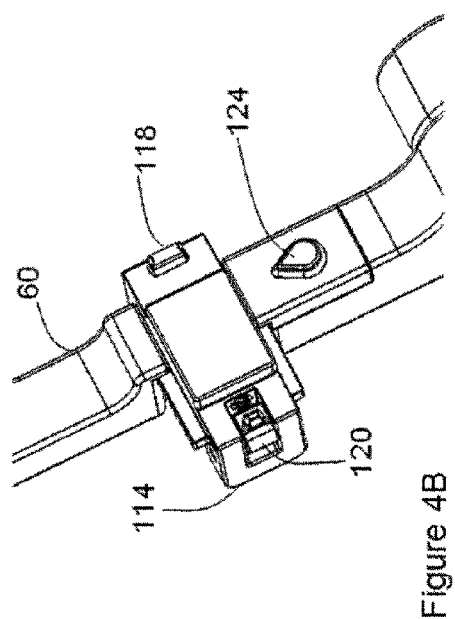
FIG. 4B schematically depicts a cassette holder of the lever of FIG. 4A in perspective view.

Lever 60 is pivotally connected to base 52, thereby enabled to move substantially up and down relative to the base. Lever 60 comprises a handle 112 physically secured to the lever, for manually moving lever 60 by a user. Lever 60 further comprises a cassette holder 114. FIG. 4A schematically depicts lever 60 without cassette holder 114, from a bottom view, that is to say a view of the side of lever 60 facing the base. FIGS. 4B and 4C schematically depict lever 60 with cassette holder 114. Cassette holder 114 is movable with respect to lever 60, and hence with respect to the base 52, in a direction perpendicular to the long dimension of biopsy needle 10. Cassette holder 114 is configured to move manually, e.g. by pressing with fingers, between two well-defined positions, for collecting two tissues from biopsy needle 10, one tissue in each well-defined position. A protruding cap 116, supported by a compression spring (not seen) is configured to apply pressure on cassette holder 114 when cassette holder 114 is assembled onto lever 60 and to hold the cassette holder in a well-defined position, when pressed into a respective depression on the side facing the lever of cassette holder 114. Two round depressions on the side facing the lever of cassette holder 114 define the two positions, respectively, for accepting the two tissues.

Figure 5:
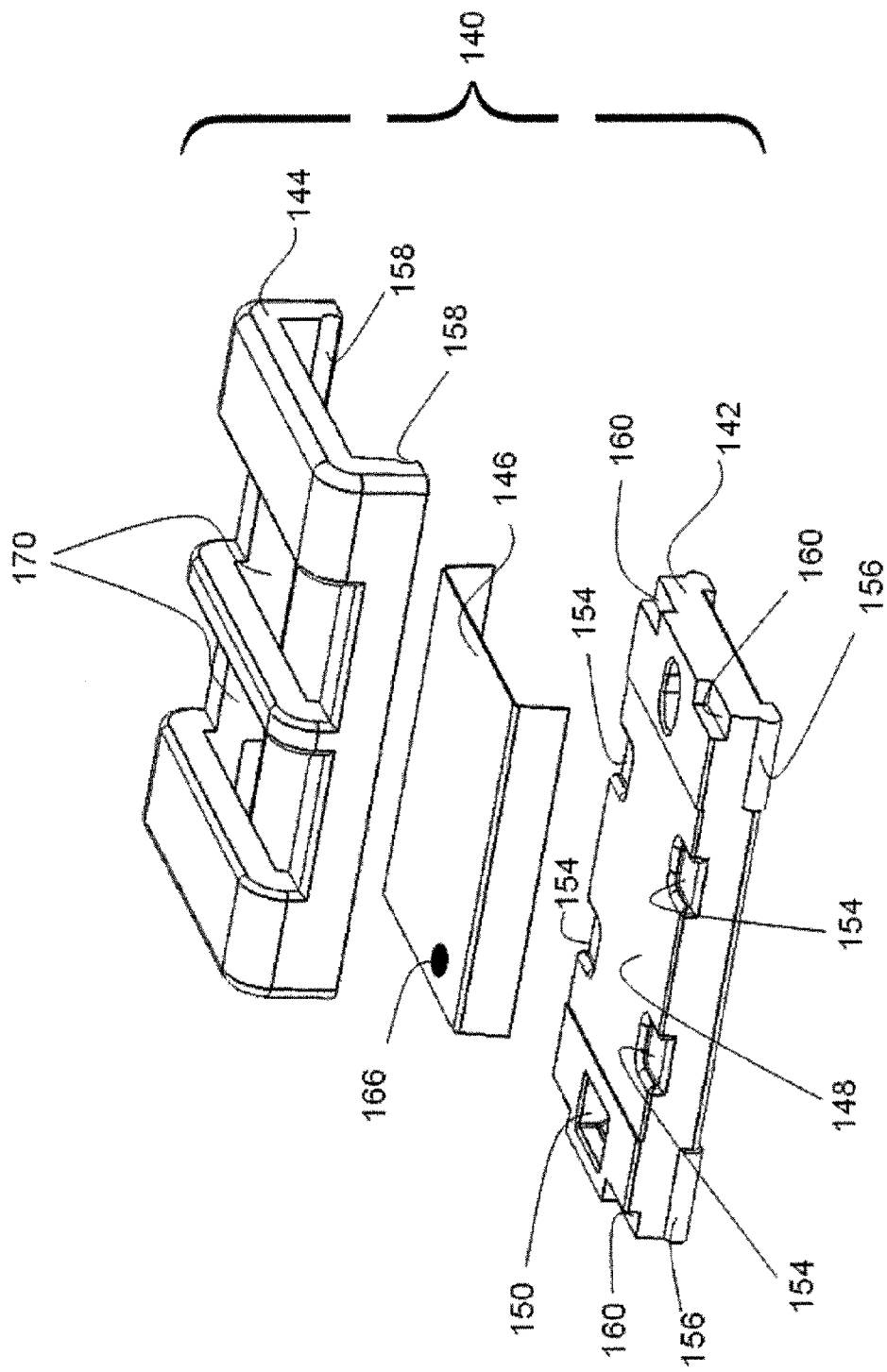
FIG. 5 schematically depicts an embodiment of a cassette usable with the tissue handling device of FIG. 3A.

Cassette holder 114 comprises a rectangular protrusion 118 and a curved tooth 120, supported by a compression spring 122, for attaching onto a cassette (140 in FIG. 5). Thereby cassette holder 114 is configured to attach to a cassette and hold it firmly, as is detailed further below. When a cassette is attached to cassette holder 114, a pointer 124 identifies for a user where on the cassette a sample tissue will be attached to.

Cassette 140 is schematically illustrated in FIG. 5. Cassette 140 comprises a cassette base 142 and a cassette cover 144, and configured to hold firmly a sample sheet 146 in between, when attached together by pressing. Cassette base 142 is a substantially rectangular slab of firm plastic material, comprising a shallow depression 148 on its upper surface for accepting sample sheet 146 thereon. The cassette base further comprises a rectangular through hole 150 on one end of the slab, and a circular through hole 152 on the other end of the slab, both together identify a left-right direction, allowing a discrimination between a first sample and a last sample taken onto the cassette. Because of circular through hole 152 and rectangular through hole 150, cassette 140 has an unsymmetrical external outline, substantially precluding rotational symmetry of the cassette, except for the trivial rotational symmetry of 360 degrees. When attached to cassette holder 114, rectangular protrusion 118 is inserted into rectangular through hole 150, and curved tooth 120 is inserted into circular through hole 152, thereby attaching the cassette to the cassette holder. Thus, Cassette base 142 further comprises four sample-edge depressions 154 on the edge of shallow depression 148. Sample-edge depressions 154 enable attachment of a long and narrow biological tissue to its full length, from biopsy needle 10, minimizing risk of losing sample ends, as is further explained below. Cassette base 142 further comprises four protrusions 156 on the sides of cassette base 142 for attaching into associated depressions 158 on the inner face of cassette cover 144, thereby attaching cassette base 142 and cassette cover 144 together.

Cassette cover 144 is a substantially rectangular slab of firm plastic material, curved to have a U shape profile. Depressions 158 on the inner side of the legs of the U are configured to attach to protrusions 156 on cassette base 142, enabling thereby attachment of cassette base 142 and cassette cover 144 together. Four corner depressions 160 facilitate detaching the cassette base from the cassette cover, e.g. for removing the sample sheet with sample tissues on it.

Cassette cover 144 comprises two rectangular windows 170 on the flat portion of the U. Rectangular windows 170 are through-openings on cassette cover 144, and when cassette 140 is assembled with sample sheet 146 held in place between cassette base 142 and cassette cover 144, windows 170 allow view and access to a portion of sample sheet 146 from the cassette cover side. The flat portions of the U maintains sample sheet 146 between cassette base 142 and cassette cover 144 flat and prevent the sample sheet from folding or bending.

Sample sheet 146 is a substantially rectangular film, folded in two rims to fit between cassette base 142 and cassette cover 144. As is schematically depicted in FIG. 6C, when cassette 140 is assembled with a sample sheet, the folded rims of the sample sheet is pressed tight between cassette base 142 and cassette cover 144, thereby preventing sample sheet from folding or bending spontaneously.

Sample sheet 146 may adhere to a biological tissue upon manually pressing on, or forming contact between the biological tissue and the sample sheet. Sample sheet 146 can further maintain such adherence, and the biological tissue remains stuck to the sample sheet following immersion in water-based solutions such as formaldehyde and during a chemical process that the sample tissue goes through in preparation to examination, as described above. Sample sheet 146 is optionally permeable to fluids, so that a fluid can permeate through sample sheet 146 from side to side. Sample sheet 146 may further be biocompatible. If a same needle is used repeatedly for obtaining several samples from the same organ, sample sheet 146 is further sterile, since during pressing the cassette with the sample sheet to the sample tissue, the biopsy needle may touch the sample sheet, and then be inserted again to the live organ to take a next sample. In some embodiments, sample sheet 146 can survive sterilization process without being damaged. In some embodiments sample sheet 146 is made of a mesh film of cellulose esters such as Immobilon-NC Transfer Membrane by Millipore™ In some embodiments sample sheet 146 is made of a film such as Mixed Cellulose Esters Membrane ME 25 or WME by Whatman Ltd. In some embodiments sample sheet 146 is made of a film such as Supor® 200 PES Membrane Disc Filter by Pall Corporation. In some embodiments sample sheet 146 is made of a film such as Cellulose Filters, for example grade 1 or grade 42 or grade 542, by Whatman Ltd. In some embodiments sample sheet 146 is a mesh film of cellulose esters covered with glue or another adhesive material so that sample tissues adhere to it. Thus, sample sheet 146 substantially comprises an adhering surface, capable of adhering to a biological tissue as described above, at least on the surface of the sample sheet that faces the sample tissue prior to collecting the tissue.

Figure 6A:
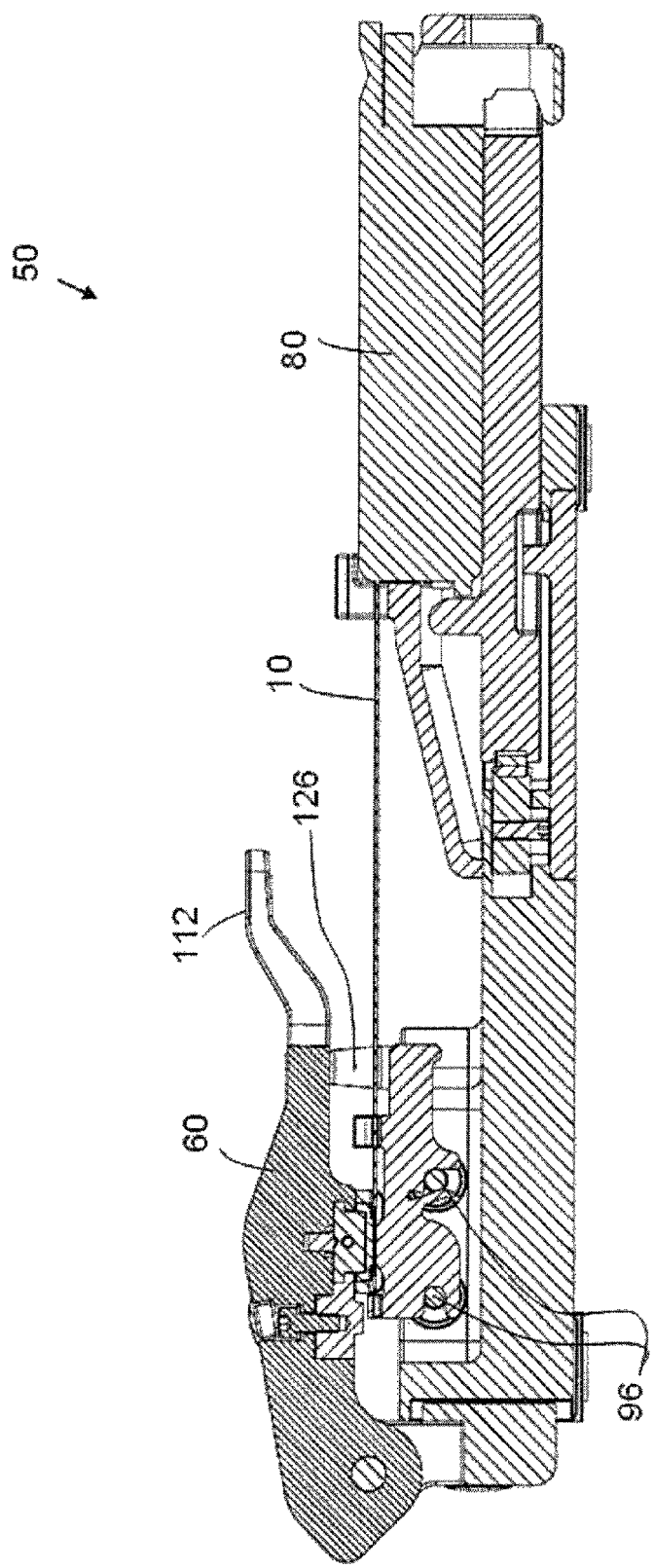
FIG. 6A schematically depicts a cross section of the tissue handling device of FIG. 3A with the lever lowered.
Figure 6B:
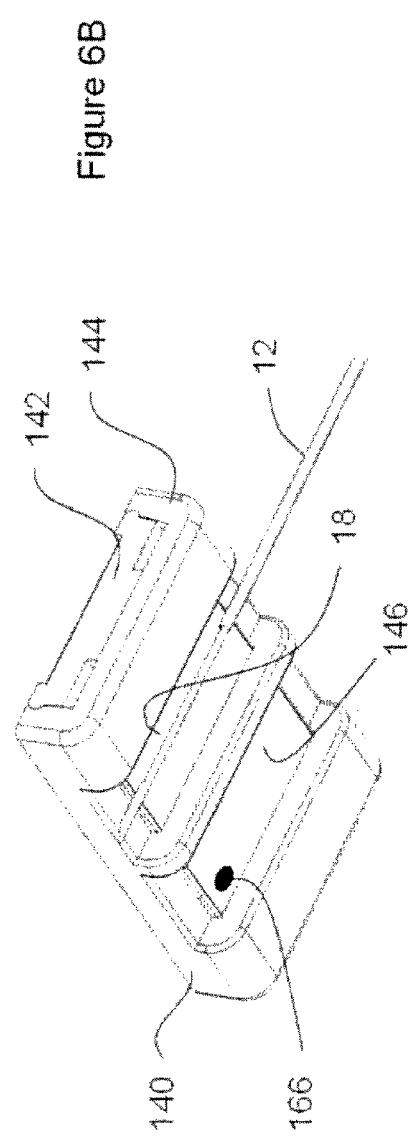
FIG. 6B schematically depicts an embodiment of a cassette attached to an embodiment of a biopsy needle.
Figure 6C:
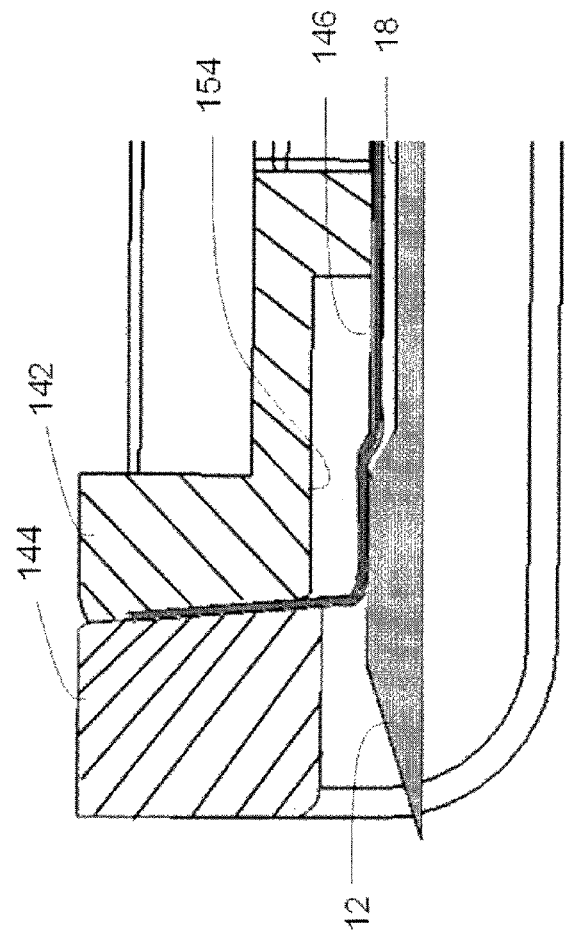
FIG. 6C schematically depicts a cassette assembled with a sample sheet with the folded rims of the sample sheet pressed tight between the cassette base and cassette cover.

For attaching a sample tissue to the sample sheet, the lever with a cassette and a sample sheet inside, is lowered onto the needle notch, as is schematically depicted in FIG. 6A. To ensure attachment of the sample tissue to the sample sheet it is required to apply some degree of pressure or sufficient contact. The pressure applied is regulated by an adjustable pin 126. Pin 126 is adjustable to control the height of lever 60 above base 52 when fully lowered, thereby defining the pressure applied by the sample sheet on the sample tissue. FIG. 6B schematically depicts sample sheet 146 inside cassette 140 touching mandrel 12 above notch 18. Sample-edge depressions 154 enable sample sheet 146 to yield as the cassette is pressed to the mandrel, thereby enabling better attachment of the sample tissue to its full length, and minimizing risk of losing sample ends as is schematically depicted in FIG. 6C.

In some embodiments, sample sheet 146 includes a mark 166, e.g. a perforated hole, chamfer edge etc, identifying one corner of the sample sheet and thus precluding the sample sheet from rotational symmetry (except for the trivial rotational symmetry of 360 degrees). When placing a new sample sheet in a cassette, the sample sheet is placed so that the mark is adjacent to a particular end of the cassette, for example adjacent to rectangular through hole 150. Mark 166 facilitates preserving the orientation of the sample tissues throughout the preparation process prior to examination, so that during examination it is known what end of the sample tissue is from far end of the notch (closest to the distal tip) and what end of the sample tissue is from near end of the notch (closest to the handle of the biopsy gun), as is further detailed and explained below regarding FIGS. 19A-19D.

Figure 19A:
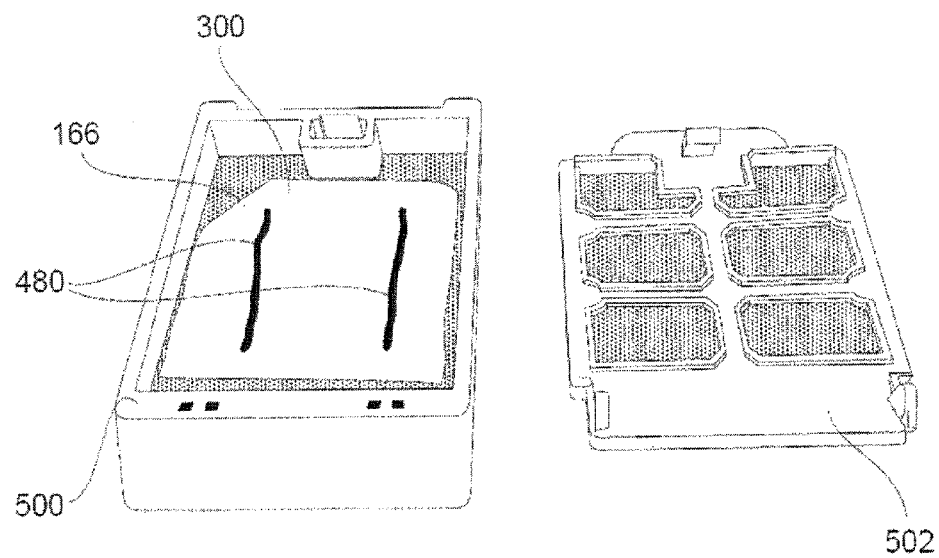
FIG. 19A schematically depicts an embodiment of a sample sheet with sample tissues in a sample box.
Figure 19B:
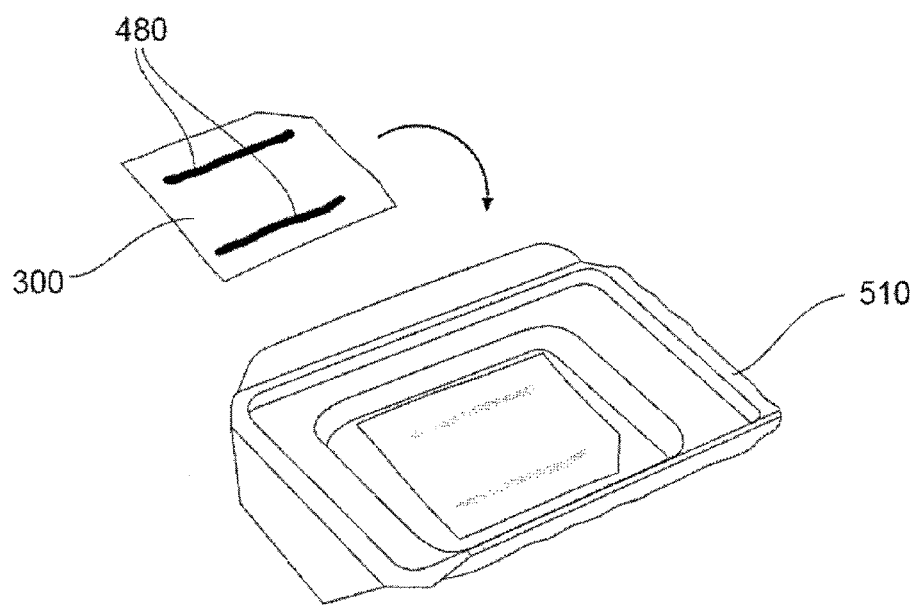
FIG. 19B schematically depicts an embodiment of a sample sheet with sample tissues in a metal mold.
Figure 19C:
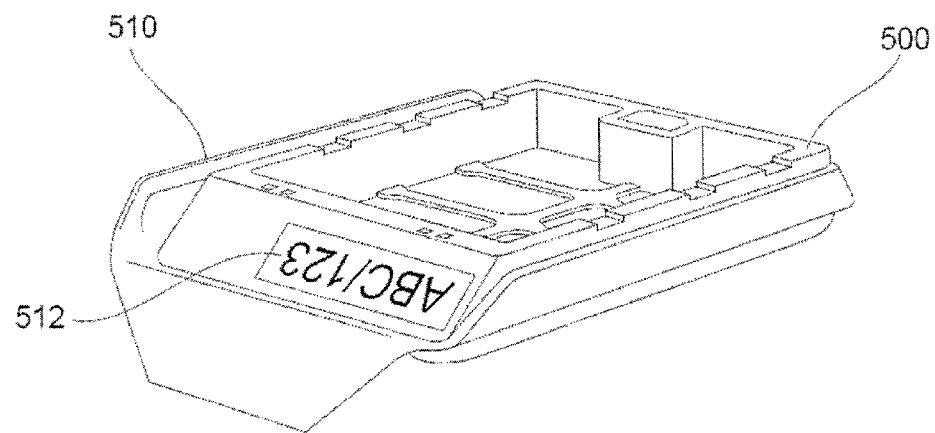
FIG. 19C schematically depicts a sample box fixed onto a metal mold.
Figure 19D:
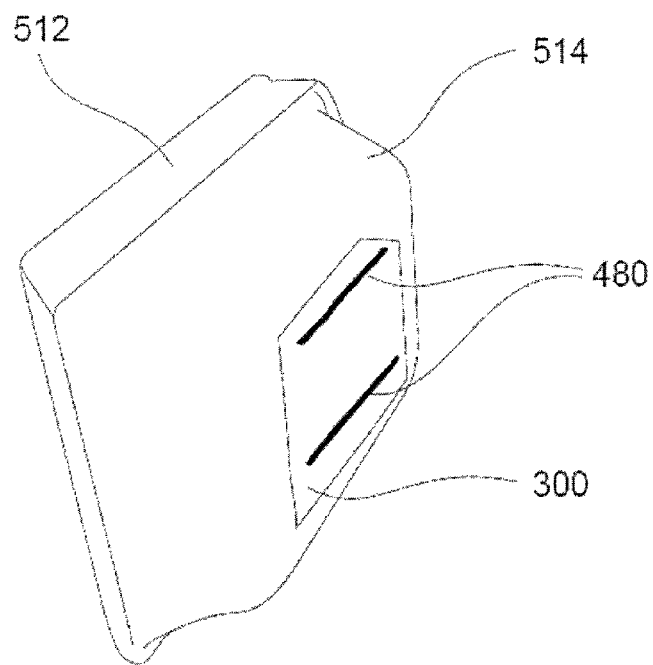
FIG. 19D schematically depicts an embodiment of a sample sheet with sample tissues in a solid paraffin block.

According to an aspect of some embodiments of the invention, there is provided a method for handling biological tissues obtained with a biopsy needle.

a. When lever 60 is lifted, an assembled cassette 140 comprising a sample sheet 146 is attached to cassette holder 114 on lever 60. A first well-defined position of the cassette holder is selected for obtaining the sample tissue on the sample sheet;

b. A biopsy gun 78 carrying a sample tissue in the exposed notch of the needle (the cannula is pulled back) is inserted to gun house 54 of tissue handling device 50, so that the needle is between alignment shoulders 90 of needle bed 58, as is explained above;

c. Sliding table 66 is pushed forward until the handle of the biopsy gun contacts front stopper 62, while the needle enters positioning sleeve 94, thereby securing the biopsy gun in the gun house;

d. Lever 60 is manually lowered until it is stopped by leveling pin 126, thereby pressing sample sheet 146 inside cassette 140 to the sample tissue on the needle and attaching the sample tissue to the sample sheet;

e. Lever 60 is lifted and the cassette holder is optionally moved to the second well-defined position for taking a second sample tissue on the same sample sheet;

f. Cassette 140 is removed from the cassette holder, the cassette is opened and the sample sheet carrying sample tissues is removed from the cassette;

g. The sample sheet carrying sample tissues 480 is placed in sample box 500, as is illustrated in FIG. 19A. The sample box is closed with sample box cover 502, and the sample tissues on the sample sheet inside the closed sample box is taken through the standard chemical preparation process prior to examination, as is described in the introduction above;

h. After the chemical preparation process, the dried sample tissues on the sample sheet is removed from the sample box and placed face down on the floor of metal mold 510, so that the sample tissues touch directly the floor of the metal mold, as is illustrated in FIG. 19B. The sample tissues are adhered to the floor of the metal mold by slight pressing, and optionally using a drop of paraffin;

i. Sample box 500 is fixed on top of metal mold 510, as is illustrated in FIG. 19C, and the space within, that is to say between the metal mold and the sample box, is filled with paraffin;

j. After the paraffin solidifies the metal mold is removed, leaving the sample box (with the marked string 512 identifying the sample tissues) filled with a block of paraffin 514 and with the sample tissue still adhered to the sample sheet, on top, as is schematically illustrated in FIG. 19D;

k. The sample box with the sample tissue is taken for slicing, as is explained above;

l. A selected slice is placed on a first glass plate and is heated and then cleaned with designated detergents to expel the paraffin. A second glass plate is then attached on top of the sample tissue, so that the sample tissue is between the first and second glass plates, and the sample tissue between two glass plates is taken for examination, e.g. under a microscope;

It is noted that mark 166 (a truncated corner in FIGS. 19A-19D) on the sample sheet preserves the orientation of the sample tissues up to and including step (j) in the method described above, that is as long as the sample tissues are adhered to the sample sheet, and before a slicing step.

According to some embodiment, orientation of the sample tissues is preserved in the slicing step (k) and paraffin melting step (l), by adequately marking the slices in step (k) and adequately marking the glass plates in step (l), so as to preserve sample tissues orientation.

According to some embodiments, the end of each sample tissue closest to mark 166 is dyed in step (j), thereby identifying orientation after slicing and paraffin melting.

According to some embodiments, a photograph of the sample tissue on the notch of the needle is taken using a photographing device such as a camera. The camera is placed e.g. at a location displaced from the mandrel perpendicularly to the axis of the biopsy needle and having line of sight with the mandrel. A photograph is taken when the biopsy gun is secured in the tissue handling device 50, in step (c) in the method above.

In some embodiments a picture is taken of the sample tissue on the sample sheet, thereby preserving the information on the position of the sample sheet relative to the sample sheet subsequent to slicing.

By recording the position of the distal tip of the needle inside the live organ while taking the sample tissue, for example by using techniques as is explained in the introduction above, the position of the distal tip of the needle at the moment of taking the sample tissue is known. By measuring, on the photograph, the distance between an end of the sample tissue and the needle distal tip, or between an end of the sample tissue and an end of the sample sheet, the position of any point on the sample tissue relative to the distal tip is known. By preserving tissue orientation until examination step (l) as explained above, any disease or tumor detected in examination is correlated to an identified end of the sample tissue. By considering the above mentioned pieces of information, a tumor or disease detected in examination can be correlated to an identified location inside the live organ from which the sample tissue was taken.

According to some embodiments a dummy sample is attached to the sample sheet at a well defined position on sample sheet 146. Consequently, in slicing step (k) above, the slices contain slices of the sample tissue (or sample tissues) and slices of the dummy sample, thus preserving orientation and position information in steps (k) and (l) in the method above. In some embodiments the dummy sample is colored or shaped so as to identify the close side to the distal tip and to identify left/right orientation of the sample sheet. In some embodiments the cassette holder of the tissue handling device is rotatable on an axis perpendicular to the plane of the sample sheet. When taking sample tissues from the biopsy needle onto the sample sheet using such a tissue handling device with a rotatable cassette holder, two tissue samples are adhered to the sample sheet in an angle. In some embodiments, two sample tissues adhered so in an angle, facilitate preserving sample orientation throughout the process until and including step (l) above.

In some embodiments the cassette holder of the tissue handling device is configured to displace linearly between well-defined positions, as cassette holder 114 above, and also to rotate on an axis perpendicular to the plane of the sample sheet. When taking sample tissues from the biopsy needle onto the sample sheet using such a tissue handling device with a linearly displaceable and rotatable cassette holder, three tissue samples may be adhered to the sample sheet in a pattern. In some embodiments, three sample tissues adhered so in a pattern, facilitate preserving sample planar orientation (rotation of the sample pattern in the plane of the sample pattern) and also up-side-down rotation, throughout the process until and including step (l) above.

An embodiment of a tissue handling device 200 as described herein is schematically depicted in FIGS. 7A-7D. Tissue handling device 200 comprises a base 202, a gun house 204, a needle bed 208 and a lever 210.

Figure 7A:
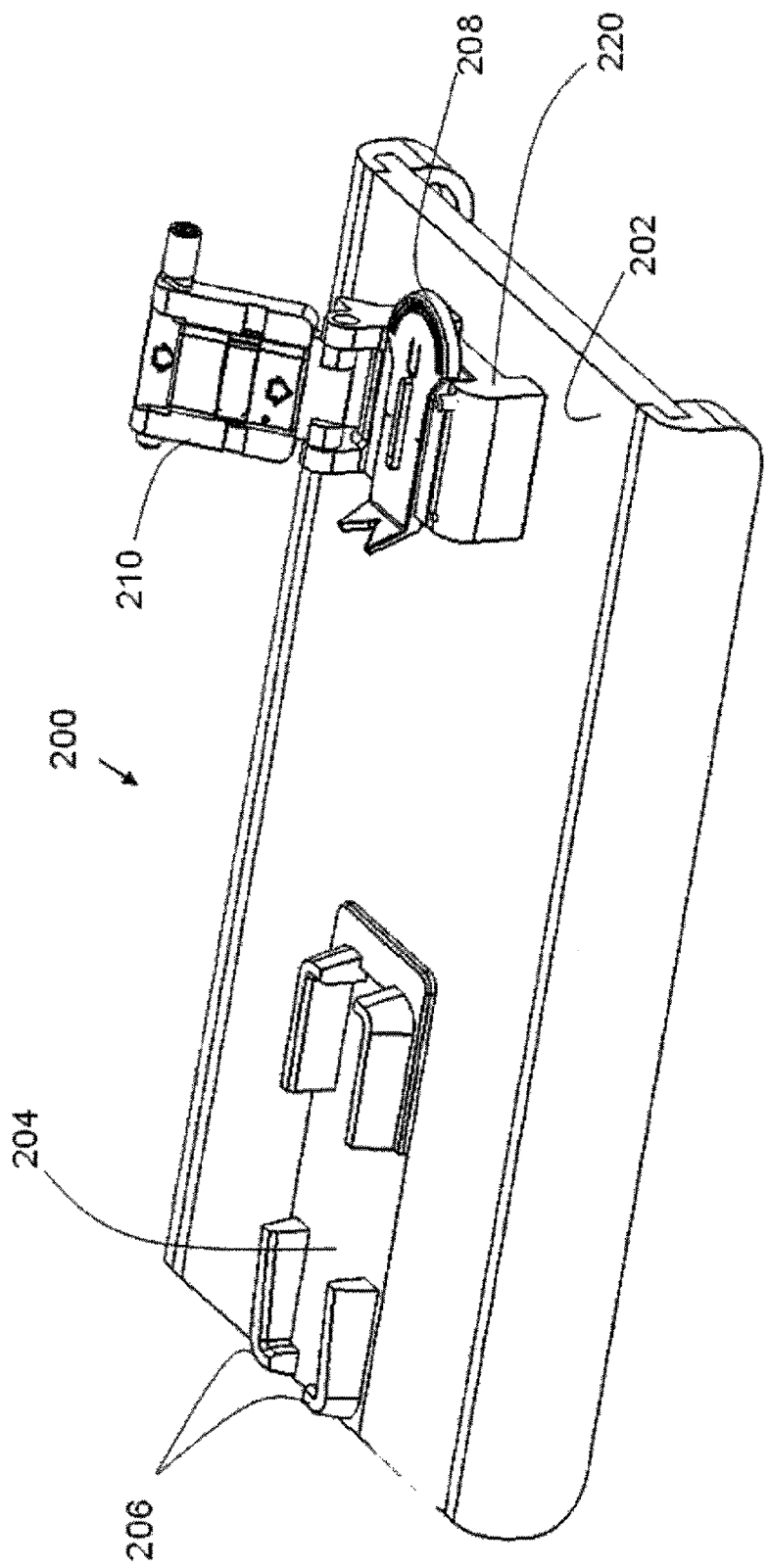
FIG. 7A schematically depicts an embodiment of a tissue handling device in a top view.
Figure 7B:
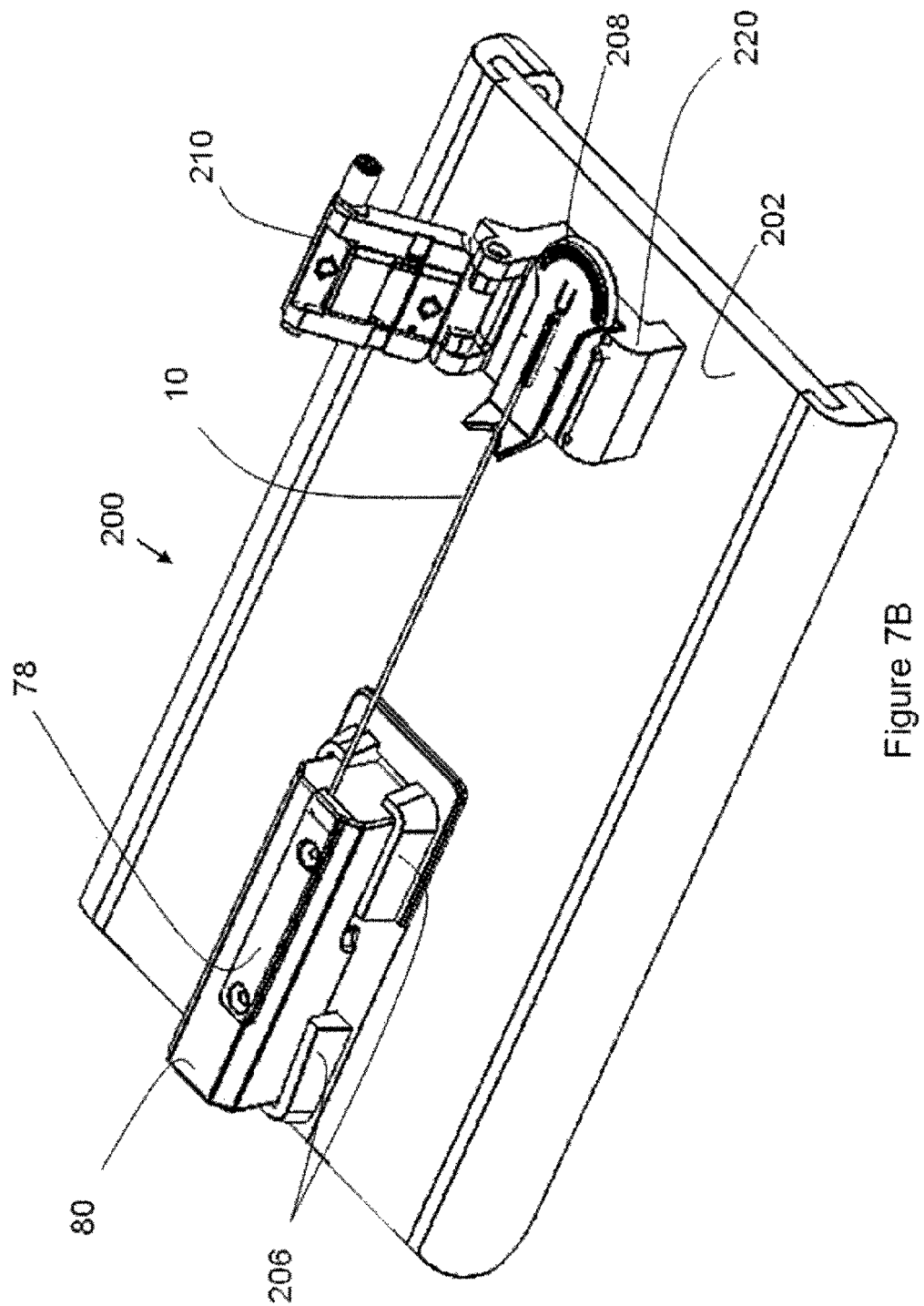
FIG. 7B schematically depicts the tissue handling device of FIG. 7A with a biopsy gun in the gun house and the lever of the tissue handling device in an open position.

Gun house 204 comprises a gun frame 206 configured for receiving therein a biopsy gun 78, having a gun handle 80 and a biopsy needle 10, as depicted schematically in FIG. 7B. Gun frame 206 has a shape and internal dimensions that fit a shape and external dimensions of gun handle 80, so that when gun handle 80 is suitably placed inside gun frame 206, biopsy gun 78 is secured in gun house 204. When biopsy gun 78 is secured in gun house 204, gun frame 206 prevents substantial movements of biopsy gun 78 sideways, forward and backwards. When biopsy gun 78 is suitably placed and secured in gun house 204, biopsy needle is supported on needle bed 208 in a substantially pre-defined position.

Figure 7C:
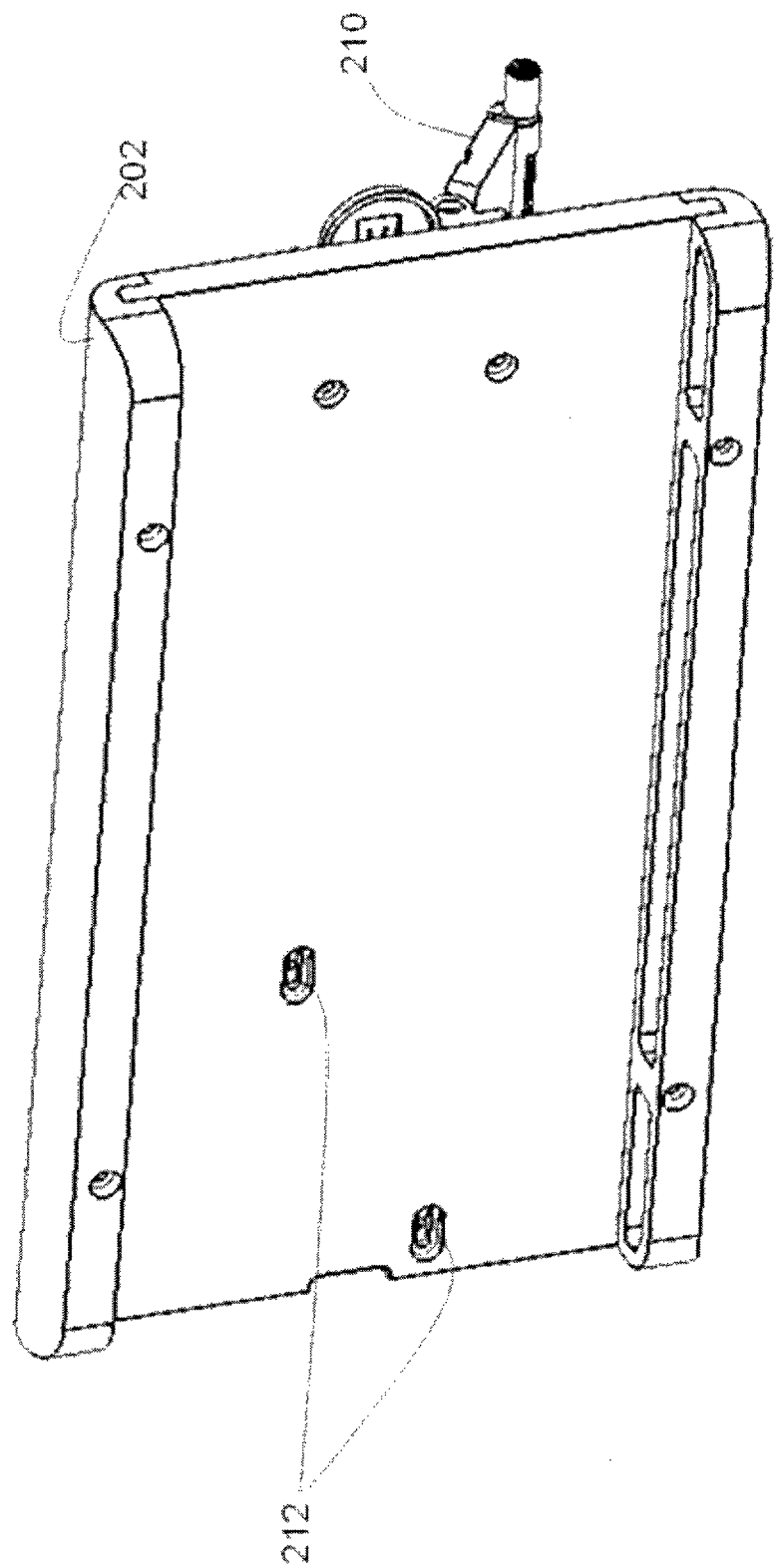
FIG. 7C schematically depicts the tissue handling device of FIG. 7A in a bottom view.

Biopsy gun 78 suitable to be secured in gun house 204 is, generally, of a particular model and having gun handle 80 of particular dimensions and shape that fit gun frame 206. When it is desired to use a tissue handling device such as tissue handling device 200 with a biopsy gun of a different model than biopsy gun 78, having a gun handle with different shape and external dimensions, a gun frame different from gun frame 206 must appropriately be used. Gun house 204 is physically secured to base 202 by two nuts 212 secured to base 202, as is schematically depicted in FIG. 7C. Thereby, when desired, gun house 204 may be replaced by another gun house having a gun frame that fits a biopsy gun different from biopsy gun 78.

Lever 210 is pivotally connected to a pedestal 220, pedestal 220 being firmly attached to base 202. Pedestal 220 is configured to support needle bed 208 at an elevated position relative to base 202, so that, when biopsy gun 78 is secured in gun house 204, biopsy needle 10 is positioned just above needle bed 208, to be supported thereon. Lever 210 is configured to be pivotally moved up and down relative to base 202, between an open position, depicted in FIG. 7B, and a closed position, depicted in FIG. 7D.

Figure 8A:
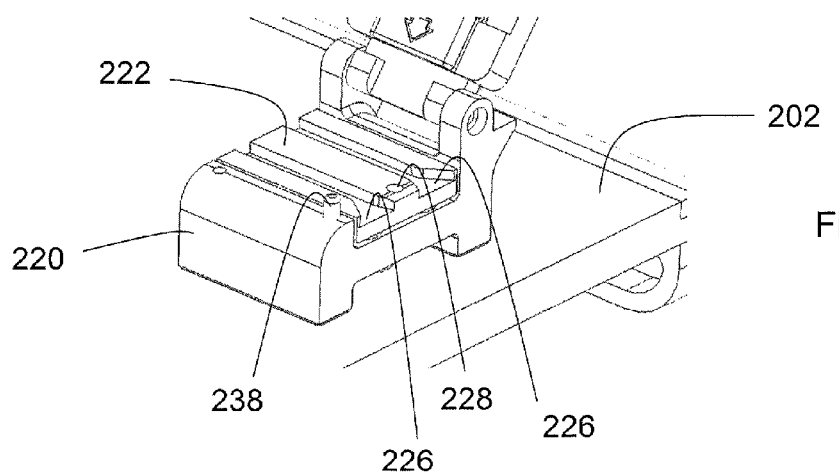
FIG. 8A schematically depicts the pedestal of the tissue handling device of FIG. 7A in perspective view.
Figure 8B:
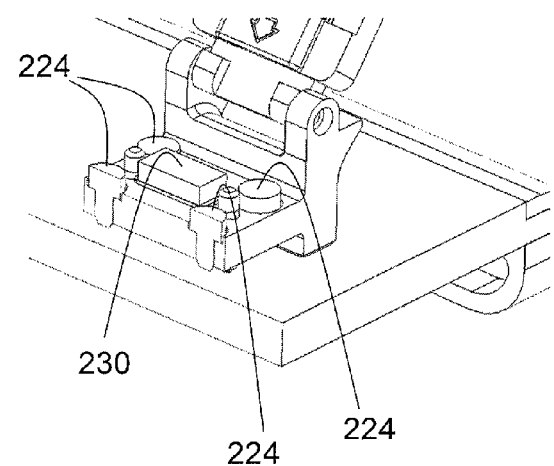
FIG. 8B schematically depicts a cross section of the pedestal of FIG. 8A in perspective view.
Figure 8C:
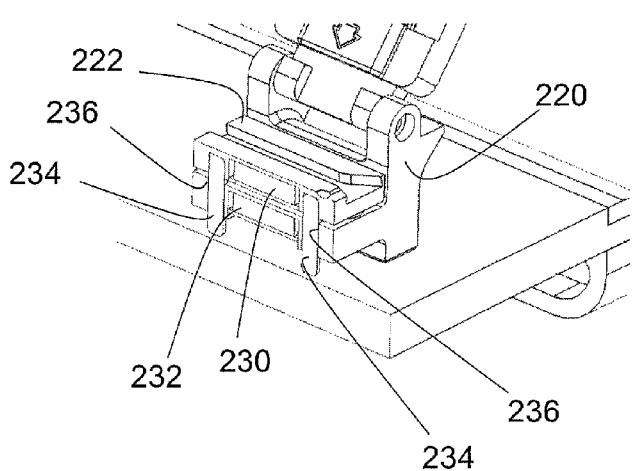
FIG. 8C schematically depicts a cross section of the pedestal of FIG. 8A in perspective view.

FIGS. 8A-8C schematically depict pedestal 220. On top of pedestal 220, a needle bed holder 222 comprises four rubber pins 224 to be supported on. Rubber pins 224 are attached in a top portion thereof to needle bed holder 222 in four blind holes (not shown) on a bottom surface of needle bed holder 222. Bottom portions of rubber pins 224 extend downwards from the bottom surface of needle bed holder 222 and are fixed inside pedestal 220. By flexibly squeezing, rubber pins 224 allow needle bed holder 222 to arrange parallel to lever 210 when lever 210 is pivotally moved downwards to a closed position, as is detailed and explained further below.

Needle bed holder 222 is a substantially rectangular slab, having two swallowtail-shaped grooves 226 and a round recess 228 on a top surface, configured to allow needle bed holder 222 to hold needle bed 208 attached thereto. FIG. 8B schematically depicts a cross-section of pedestal 220 in a plane passing through two rubber pins 224. In FIG. 8B a top surface of needle bed holder 222 is not shown, exposing the top portion of rubber pins 224 and an internal configuration of needle bed holder 222.

FIG. 8C schematically depicts a cross-section of pedestal 220 in a vertical plane passing through the center of needle bed holder 222. Needle bed holder 222 comprises a top magnet 230 inside an internal hollow compartment, and pedestal 220 comprises a bottom magnet 232 in an internal hollow compartment thereof. When needle bed holder 222 is arranged in place, supported by rubber pins 224, top magnet 230 and bottom magnet 232 generate a mutual magnetic attraction force, that attracts needle bed holder 222 onto pedestal 220, thereby assisting in stabilizing needle bed holder 222 on rubber pins 224.

Needle bed holder 222 further comprises rigid pins 234 fixed inside needle bed holder 222 and having a bottom part thereof projecting downwards from needle bed holder 222. Pedestal 220 comprises two through holes 236, arranged to fit rigid pins 234. Through holes 236 have a diameter larger than the diameter of rigid pins 234, so that rigid pins 234 do not substantially restrict needle bed holder 222 from tilting on top of rubber pins 224, yet rigid pins 234 restrict needle bed holder 222 from substantially displacing horizontally, thereby assisting stabilizing needle bed holder 222 on rubber pins 224 against horizontal displacements. In some embodiments through holes 236 may have a diameter larger than the diameter of rigid pins 234 by about 0.1 mm-1 mm, for example by about 0.3 mm, by about 0.5 mm and even by about 0.8 mm. In some embodiments, rigid pins 234 may have different diameters from one another, and through holes 236 may have different diameters from one another respectively, thereby compelling assembly of needle bed holder 222 onto pedestal 220 in a single orientation.

Pedestal 220 further comprises a stopper pillar 238 extending upwards towards lever 210. Lever 210 may be lowered towards a closed position until lever 210 is stopped by stopper pillar 238, stopper pillar 238 thereby sets the position of lever 210 above pedestal 220 in a closed position. Some embodiments of pedestal 220 may not comprise stopper pillar 238, in which embodiments pressing lever 210 downwards to a closed position may apply pressure on rubber pins 224, but nevertheless may not apply pressure on a sample tissue or flatten a sample tissue, as is further explained below.

Figure 9A:
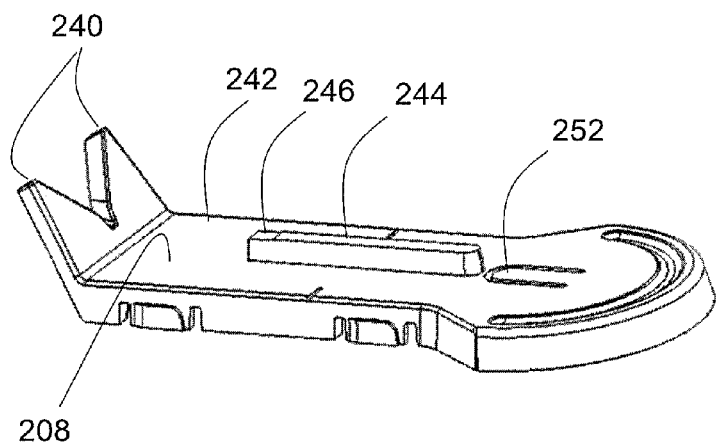
FIG. 9A schematically depicts the needle bed of the tissue handling device of FIG. 7A in perspective view from the top.
Figure 9B:
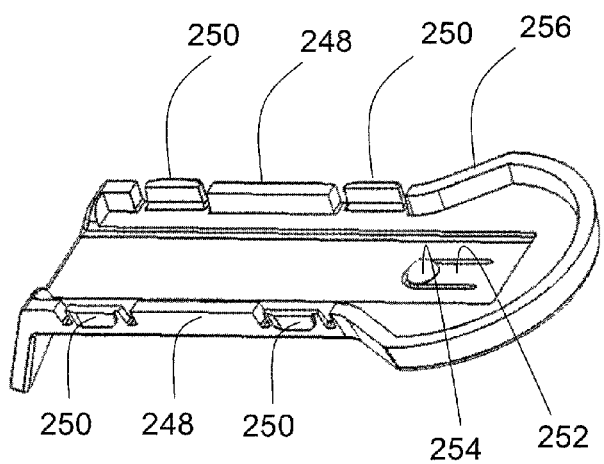
FIG. 9B schematically depicts the needle bed of FIG. 9A in perspective view from the bottom.

FIG. 9A schematically depict needle bed 208 from a top perspective view. Needle bed 208 comprises two alignment shoulders 240 and a support platform 244, aligned along the center line of needle bed 208, on a top surface 242. A descended step 246 on the near end (that is to say the end closer to gun house 204) of support platform 244 is descendent relative to support platform 244 thereby being configured to support the cannula 14 of a biopsy needle 10, whereas support platform 244 supports the mandrel 12, having a smaller diameter than the cannula. FIG. 9B schematically depicts needle bed 208 from a bottom view. Needle bed 208 comprises bed slides 248 along the two rims of a bottom surface thereof and further comprises bulges 250 on bed slides 248. Needle bed 208 further comprises a flexible leaf 252 having a round protrusion 254 at the free end of the leaf.

In use, needle bed 208 may be exposed to body fluids due to contact with the biopsy needle, and therefore may need to be replaced after a last sample tissue is taken from the live organ in a biopsy session. Needle bed 208 is therefore configured to be quickly assembled to, and disassembled from, needle bed holder 222, by hand. Needle bed 208 is assembled onto needle bed holder 222 by inserting bed slides 248 to swallowtail grooves 226 and sliding needle bed 208 horizontally until stopper 256 on the bottom surface of needle bed 208 touches a respective portion of swallowtail grooves 226 and stops further displacement of needle bed 208. While sliding needle bed 208 onto needle bed holder 222, rigid pins 234 restrict horizontal displacement of needle bed holder 222, as described above, thereby facilitating assembly. When needle bed 208 is so assembled onto needle bed holder 222, bulges 250 are configured to chafe against swallowtail grooves 226 of needle bed holder 222, thereby assisting in stabilizing needle bed 208 in place. Further, when needle bed 208 is assembled onto needle bed holder 222 by sliding all the way through and stopper 256 stops further displacement of needle bed 208, round protrusion 254 on leaf 252 enters round recess 228 on needle bed holder 222, thereby assisting in fixing needle bed 208 on needle bed holder 222.

Figure 9C:
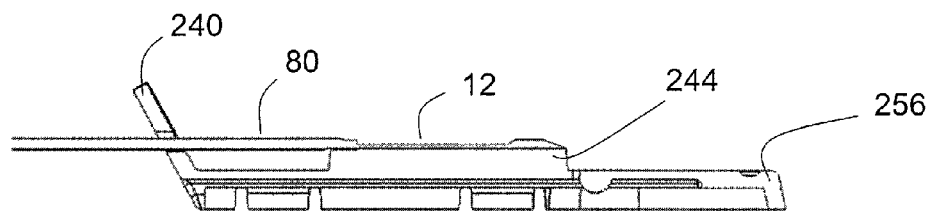
FIG. 9C schematically depicts a side view of the needle bed of FIG. 9A.

FIG. 9C schematically depicts a cross section of needle bed 208 in a vertical plane through biopsy needle 10. When needle bed 208 is assembled in tissue handling device 200 and biopsy gun 78 is placed in gun house 204, biopsy needle 10 is arranged on top of support platform 244, and support platform 244 supports biopsy needle 10 in a position pre-defined by gun house 204 and by alignment shoulders 240.

Figure 10A:
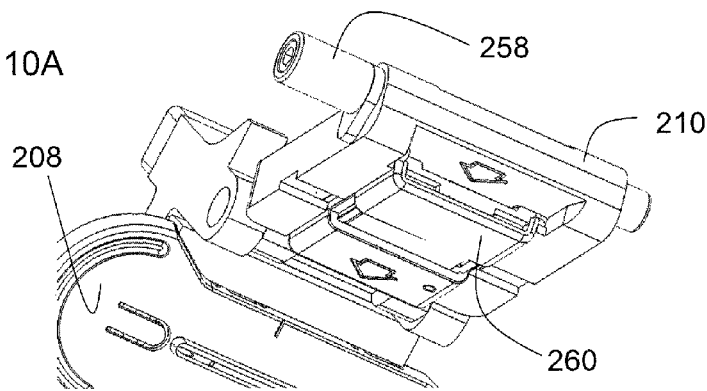
FIG. 10A schematically depicts the lever of the tissue handling device of FIG. 7A with an assembled cassette.

Lever 210 is depicted schematically in FIGS. 10A-10D in a perspective view, depicting the side that faces base 202 when lever 210 is moved down to a closed position. FIG. 10A schematically depicts lever 210 pivotally connected to pedestal 220, thereby enabled to move substantially up and down relative to base 202. Lever 210 comprises a handle 258 physically associated with lever 210, for manually moving lever 210 by a user. Lever 210 is further configured to attach to a cassette 260, cassette 260 being used for receiving sample tissues from biopsy needle 10 and for facilitating handling such sample tissues.

Figure 10B:
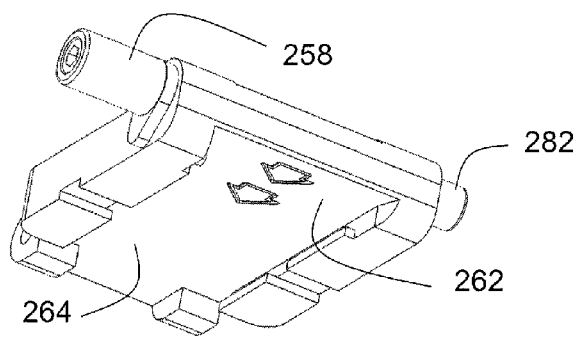
FIG. 10B schematically depicts the lever of FIG. 10A without a cassette.
Figure 10C:
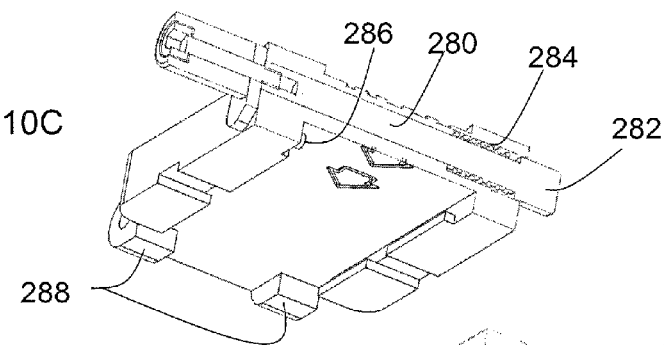
FIG. 10C schematically depicts a cross section through the handle of the lever of FIG. 10B.
Figure 10D:
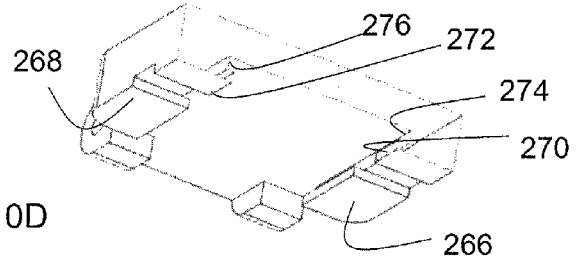
FIG. 10D schematically depicts a cross section of the lever of FIG. 10B.

FIGS. 10B-10D schematically depict lever 210 without cassette 260. Lever 210 comprises a cassette house 262 configured to attach to cassette 260 as is explained below. Cassette house 262 comprises a cassette surface 264 descended between a first elevated rim 266 and a second elevated rim 268 depicted in cross-sectional view 5D. A first protrusion 270 and a second protrusion 272 protrude from the first elevated rim and from the second elevated rim, respectively, towards cassette surface 264, thereby forming a first groove 274 and second groove 276 configured for cassette attachment as is explained further below. First protrusion 270 is wider than second protrusion 272, namely first protrusion 270 protrudes more, respectively, than second protrusion 272, thereby forming left-right asymmetry of cassette house 262, due to a deeper first groove 274 relative to second groove 276. An asymmetry of cassette house 262, together with a respective asymmetry of cassette 260, compels a single orientation of attachment of cassette 260 in cassette house 262, thereby retaining orientation of a sample tissue taken for inspection and attached to cassette 260, as is further detailed below.

Lever 210 further comprises a cassette back stopper 280, comprising a depressable pin 282 physically associated with a compression spring 284 and with a back stopper pin 286. FIG. 10C schematically depicts lever 210 in cross-sectional view through cassette back stopper 280. For inserting cassette 260 to cassette house 262 for attachment therein, depressable pin 282 is depressed, e.g. by fingers, thereby pushing back stopper pin 286 into second groove 276, and allowing sliding cassette 260 into second groove 276 and first groove 274. Cassette 260 may be so slid into cassette house 262 until cassette 260 is stopped by front stoppers 288. When depressable pin 282 is released, compression spring 284 restores back stopper pin 286 (and depressable pin 282) to the former protruding position, thereby securing cassette 260 in cassette house 262. When cassette 260 is attached to lever 210 in cassette house 262, cassette 260 is allowed to slide in cassette house 262 back and forth between front stoppers 288 and back stopper pin 286, thereby allowing collecting more than one sample tissue onto cassette 260, as is explained further below.

Figures 11A, 11B, 11C:
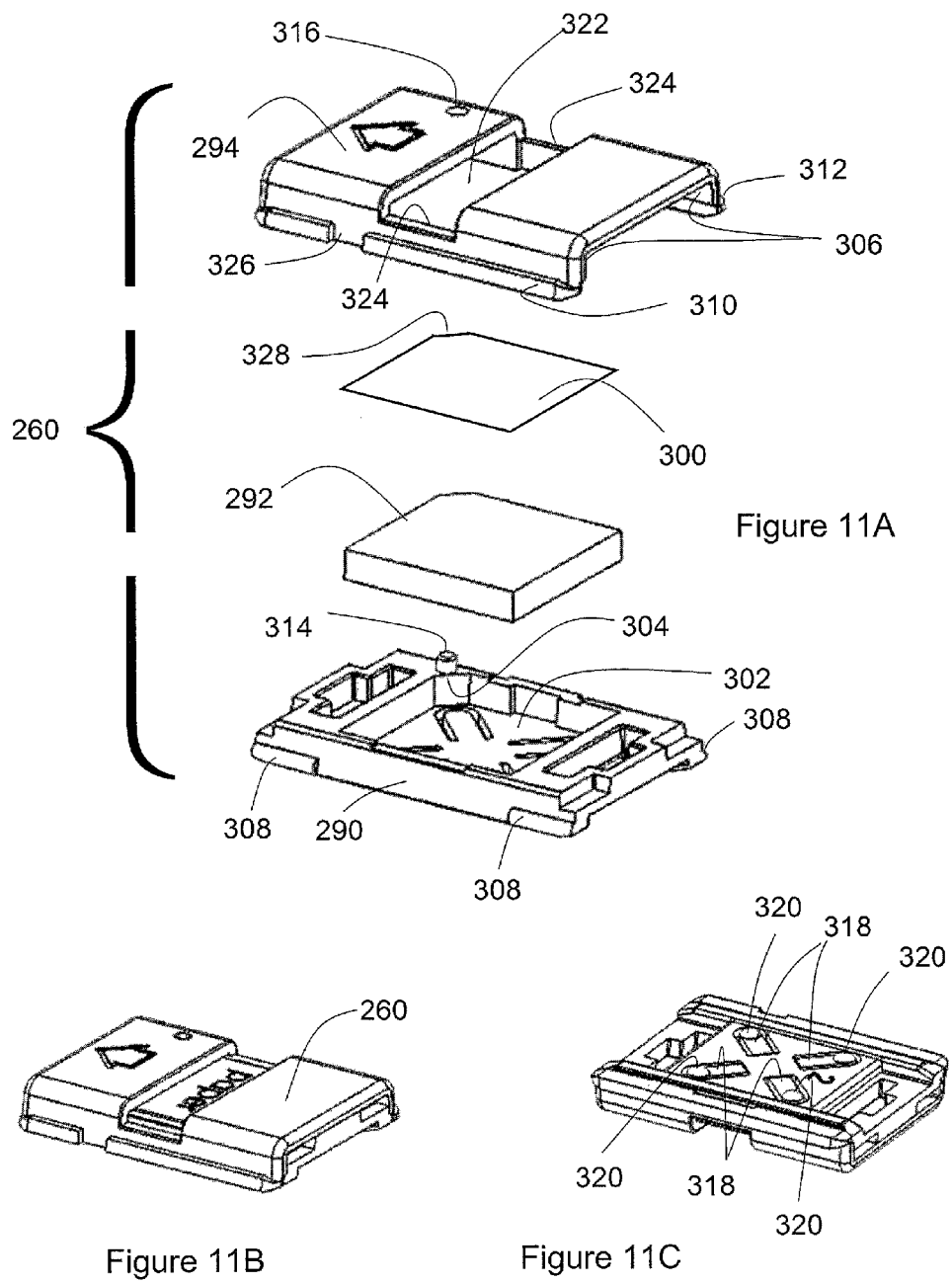
FIG. 11A schematically depicts an embodiment of a cassette usable with the tissue handling device of FIG. 7A, in an exploded view.
FIG. 11B schematically depicts the cassette of FIG. 11A, in perspective view from the top.
FIG. 11C schematically depicts the cassette of FIG. 11A, in perspective view from the bottom.

FIG. 11A schematically depicts cassette 260 in an exploded view; FIG. 11B schematically depicts cassette 260 in a top view and FIG. 11C schematically depicts cassette 260 in a bottom view. Cassette 260 comprises a cassette base 290, a sponge 292 and a cassette cover 294. Cassette 260 is configured to further include and hold a sample sheet 300. Cassette base 290 is a substantially rectangular slab e.g. of firm plastic material, comprising a hollow compartment 302 on its surface facing cassette cover 294, for including sponge 292 therein. Compartment 302 has a substantially rectangular periphery having a truncated corner 304. Sponge 292 has periphery substantially similar to that of compartment 302, having a rectangular shape with a truncated corner. Sponge 292 is made of a soft and flexible material, for suitably yielding and supporting sample sheet 300 when attaching a sample tissue thereon, as is further described below. Yielding herein means retreating flexibly in response to pressure, thereby enabling returning to a previous position when such pressure is stopped. Cassette cover 294 is a substantially rectangular slab e.g. of firm plastic material, curved to have a U shape profile. Cassette cover 294 comprises depressions 306 on the inner side of the legs of the U, configured to attach to protrusions 308 on cassette base 290, enabling thereby attachment of cassette base 290 and cassette cover 294 by pressing. When cassette 260 is assembled with sample sheet 300, sample sheet 300 is held pressed between cassette cover 294 and sponge 292 thereby being prevented from displacing, folding or bending spontaneously.

Cassette base 290 further comprises a protruding pin 314 extending upwards from the surface of cassette base 290 facing cassette cover 294. Cassette cover 294 comprises an alignment hole 316, arranged to fit to protruding pin 314. For assembly of cassette 260, protruding pin 314 must be inserted into alignment hole 316. Protruding pin 314 and alignment hole 316 thus compel a single orientation of assembly of cassette cover 294 onto cassette base 290.

Cassette cover 294 further comprises a first slide 310 on the outside of one leg of the U, and a second slide 312 on the other leg of the U, for allowing sliding cassette 260 into cassette house 262 for attachment therein. First slide 310 is wider than second slide 312, thereby fitting first groove 274 and second groove 276, respectively, and forming a left-right asymmetry in cassette 260 fitting to the left-right asymmetry of cassette house 262 described above.

Cassette base 290 comprises four flexible leafs 318, each having a bulge 320 protruding outwards on the free end of the leaf. When cassette 260 is inserted into cassette house 262, bulges 320 chafe on cassette surface 264, thereby preventing free displacements of cassette 260 in cassette house 262, and assisting stabilizing cassette 260 therein. Further, flexible leafs 318 enable cassette 260 to tilt in cassette house 262, to an amount dictated by a gap between slides 310 and 312 and grooves 274 and 276, respectively, thereby assisting in stabilizing cassette 260 parallel to a biopsy needle supported on support platform 244, when cassette 260 is pressed towards the biopsy needle.

Cassette cover 294 comprises a window 322 for allowing view and access to a portion of sample sheet 300 inside cassette 260. In use, sample tissues may be attached to sample sheet 300 on the area of window 322. Window 322 has side edges 324.

First slide 310 of cassette cover 294 is split by a gap 326 which is employed to discriminate first slide 310 from second slide 312 in subsequent process steps as is described further below.

Sample sheet 300 may be for example a film having a substantially rectangular shape with a sheet truncated corner 328, fitting in shape and dimensions to compartment 302 in cassette base 290. For assembly of cassette 260 with a sample sheet, sponge 292 is inserted to compartment 302 of cassette base 290, sample sheet 300 is placed on top of sponge 292 and cassette cover 294 is pressed onto cassette base 290, to form assembled cassette 260 as is schematically depicted in FIG. 11B. When assembled, cassette 260 holds sample sheet 300 pressed between sponge 292 and cassette cover 294. Truncated corner 304 of compartment 302 and protruding pin 314 compel assembly of sample sheet 300 in a single orientation so that sheet truncated corner 328 of sample sheet 300 is adjacent truncated corner 304 of compartment 302.

Thus, sample sheet 300 is precluded of rotation symmetry, except of the trivial rotational symmetry of 360 degrees, due to truncated corner 328. Further, cassette 260 has an internal structure which is compatible with the unsymmetrical structure of sample sheet 260, thus compelling assembly of sample sheet 300 in cassette 260 and holding sample sheet 300 therein, in a single orientation. The orientation of sample sheet 300 relative to cassette base 290 is unique because sheet truncated corner 328 of sample sheet 300 must fit truncated corner 304 of compartment 302; the orientation of cassette base 290 relative to cassette cover 294 is unique due to protruding pin 314 and alignment hole 316; and the orientation of cassette 260 relative to lever 210 and thereby to biopsy needle 10 (in FIG. 7B) is unique because of first slide 310 and second slide 312 on cassette cover 294, and first groove 274 and second groove 276 on lever 210, respectively. Consequently, the arrangement of cassette 260 relative to needle bed 208 is pre-defined and unique in the closed position of lever 210. Hence, the orientation of sample sheet 300 relative to the notch of biopsy needle 10, while attaching a sample tissue to sample sheet 300, is unique, and the end of the sample tissue that is closer to sheet truncated corner 328 on sample sheet 300 is the end that was closer to the handle of the biopsy gun and distant from the distal tip of the biopsy needle. Therefore, the orientation of the sample tissue is known and maintained as long as the sample tissue is attached to sample sheet 300.

Sample sheet 300 may adhere to a biological tissue upon manually pressing on, or forming contact between the biological tissue and the sample sheet. Sample sheet 300 can further maintain such adherence, and the biological tissue remains stuck to the sample sheet following immersion in water-based solutions such as formaldehyde and during a chemical process that the sample tissue goes through in preparation to examination, as described above. Sample sheet 300 is substantially similar to sample sheet 146 described above in all the characteristics involving adherence to a biological tissue and further in characteristics corresponding to affecting the sample tissue. Specifically, sample sheet 300 comprises an adhering surface capable of adhering to a biological tissue at least on the surface of the sample sheet that faces the sample tissue prior to collecting the sample tissue onto the sample sheet as described above.

In use of tissue handling device 200 and for attaching a sample tissue to sample sheet 300, cassette 260 is assembled with sample sheet 300 and inserted to cassette house 262 in lever 210, as is described above. A user may select a position on sample sheet 300 where a sample tissue would adhere, by selecting a position of cassette 260 relative to lever 210, between back stopper pin 286 and front stoppers 288. In some embodiments at least two such positions of cassette 260 are enabled, allowing attaching at least two sample tissues on a same sample sheet 300. In some embodiments several such positions of cassette 260 are enabled, allowing attaching several sample tissues on a same sample sheet 300.

Biopsy gun 78, including a sample tissue in the notch of biopsy needle 10, is placed in gun house 204 so that the notch of biopsy needle 10 is facing upwards, towards lever 210. Biopsy needle 10 is positioned between alignment shoulders 240 and supported on support platform 244 of needle bed 208, as is depicted in FIG. 7B. Top magnet 230 in needle bed holder 222 (FIG. 8C) may apply a magnetic force on biopsy needle 10, attracting biopsy needle 10 downwards towards support platform 244 and assisting stabilizing biopsy needle 10 thereon. The position of the distal tip of biopsy needle 10 on support platform 244, e.g. along the long dimension of biopsy needle 10, may be adjusted by a user by releasing nuts 212 (FIG. 7C), adjusting the position and orientation of gun house 204 and tightening nuts 212 again.

Figure 7D:
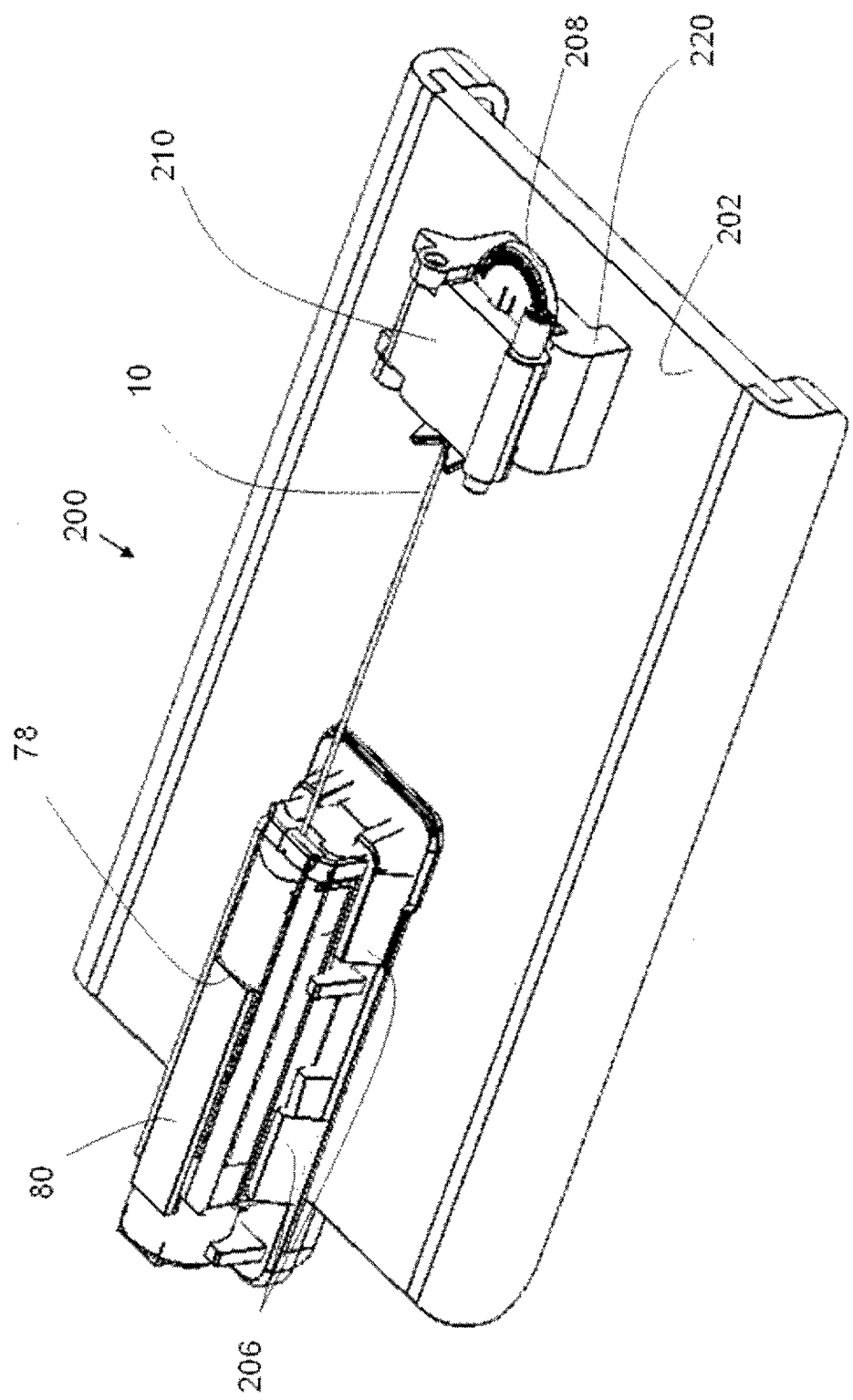
FIG. 7D schematically depicts the tissue handling device of FIG. 7A with a biopsy gun in the gun house and the lever of the tissue handling device in a closed position.

Lever 210 is lowered, e.g. by hand, to a closed position as is schematically depicted in FIG. 7D. When sample sheet 300 is brought to contact with the sample tissue in the notch of biopsy needle 10, the sample tissue adheres to sample sheet 300. Lever 210 may then be lifted to an open position and the user may select to displace cassette 260 to a new position on lever 210 and take a next sample tissue thereon, or to disassemble cassette 260 from lever 210, to disassemble sample sheet 300 from cassette 260 and take sample sheet 300 with the sample tissue thereon for further process.

FIG. 12 schematically depicts a cross-section of tissue handling device 200 in a closed position, in a vertical plane along biopsy needle 10, depicting lever 210 and pedestal 220. When lever 210 is lowered towards a closed position, the notch 18 of biopsy needle 10 is facing window 322 of cassette 260, and cassette base 290, near window edges 324 touch biopsy needle 10 preferably on both sides of the notch. Lever 210 may be lowered further until lever 210 is stopped by stopper pillar 238. Lowering lever 210 beyond the point at which cassette base 290 touch biopsy needle 10 applies a downwards force on biopsy needle 10 and on needle bed 208 and needle bed holder 222 supporting biopsy needle 10. Rubber pins 224 (not shown in this Figure) may thus yield by squeezing, allowing lever 210 to lower further until being stopped by stopper pillar 238.

Yielding of rubber pins 224 and bulges 320 on cassette base 290 as described above assists in compensating possible deviation from parallelism between cassette 260 and biopsy needle 10. Such deviation from parallelism may occur e.g. due to accumulation of mechanical tolerances between cassette 260 and lever 210, lever 210 and pedestal 220, pedestal 220 and needle bed holder 222 and needle bed holder 222 and needle bed 208. Further, it may occur that biopsy needle 10 might be bent (particularly in a vertical plane) resulting in a deviation from parallelism between cassette 260 and biopsy needle 10 even in a hypothetical case of an ideal mechanical configuration of tissue handling device 200 and absolute parallelism between cassette 260 and needle bed 208. By pressing biopsy needle 10 downward by applying a downward force by lever 210 on biopsy needle 10 as described above, and by rubber pins 224 yielding flexibly to such downward force, needle bed 208 and consequently biopsy needle may tilt and align parallel to cassette 260, thereby allowing a suitable contact between the sample tissue on the notch and sample sheet 300 in cassette 260. In some embodiments rubber pins 224 may yield by squeezing as described above over a distance in the range of 0-5 mm. In some embodiments such distance may be 0 mm, 1 mm and even 5 mm. In some embodiments a mechanism other than rubber pins 224 is contemplated that enables needle bed 208, and consequently biopsy needle 10, to tilt, and possibly to yield, so as to align in parallel to cassette 260; for example a mechanism including a single spring, a multitude of springs, a single bulk of soft and flexible material such as a sponge, or a mechanism including a ball joint, or any other suitable mechanism as known in the art.

A typical biopsy sample tissue taken by a biopsy needle and positioned on the needle's notch may have an uneven thickness, that is to say the sample tissue's profile along the notch may deviate significantly from a straight line, having typical "hills" and "valleys". To ensure continuous adherence of the sample tissue to sample sheet 300 along the length of the sample tissue, continuous contact should be formed, possibly necessitating pressing down protruding portions of the sample tissue, to reach thin, or low-profile portions thereof. However pressing down thick portions of sample tissue, resulting in flattening the sample tissue, is generally undesired, because flat and thin sample tissues on the sample sheet may provide a small number of slices or sections for a later inspection e.g. under a microscope.

Sponge 292 in cassette 260 flexibly supports sample sheet 300, so as to enable contact with thin portions of the sample sheet and reduce the amount of pressing down thicker portions of the sample. When cassette base 290 near window edges 324 of cassette 260 touch biopsy needle 10, sample sheet 300, supported by sponge 292, is configured to enter into the notch to increase sample tissue collection efficiency. In some embodiments sample sheet 300, supported by sponge 292, is configured to enter into the notch a distance in the range of 0-1 mm, for example enter into the notch by about 0.2 mm. In some embodiments sample sheet 300, supported by sponge 292, is configured to enter into the notch and reach a distance in the range of 0-1 mm above the notch floor, for example reach a distance of about 0.3 mm above the notch floor. Sample sheet 300 reaching such a small distance above the notch floor may ensure adherence of sample tissue portions that are thicker than 0.3 mm, thereby minimizing amount of sample tissue left on the notch and increasing considerably sample tissue collection efficiency. Flexible support of sample sheet 300 by sponge 292 allows sample sheet 300 to yield at regions where thick portions of the sample tissue contact sample sheet 300, thereby reducing amount of pressing and flattening such thicker portions of the sample tissue. Further, Flexible support of sample sheet 300 by sponge 292 allows sample sheet 300 to yield at the ends of the notch, thereby allowing sample sheet 300 to enter into the notch in the vicinity of notch ends, thereby allowing collection of sample tissue from the regions of the notch ends. Thus, flexible support of sample sheet 300 by sponge 292 allows maximizing collection efficiency of sample tissue from the notch by reaching sample tissue near notch ends and by reaching thin portions of sample tissue, while flattening thick portions of sample tissue is restricted, thereby retaining thickness of thick sample tissue portions for subsequent inspecting steps.

It is noted that in some embodiments the orientation of a biopsy gun relative to base 202 may be different from that which is described above in FIGS. 7-12, for example the biopsy gun may be oriented so that the notch faces sideways rather than upwards. Three embodiments comprising three different mutual orientations, respectively, of notch 18, supporting a sample tissue, relative to sample sheet 300, are schematically depicted in FIGS. 13A, 13B and 13C. When lever 210 is lowered to a closed position, sample sheet 300 is substantially perpendicular to the notch floor, and consequently the sample tissue is not pressed between sample sheet 300 and the notch floor.

Figure 14A:
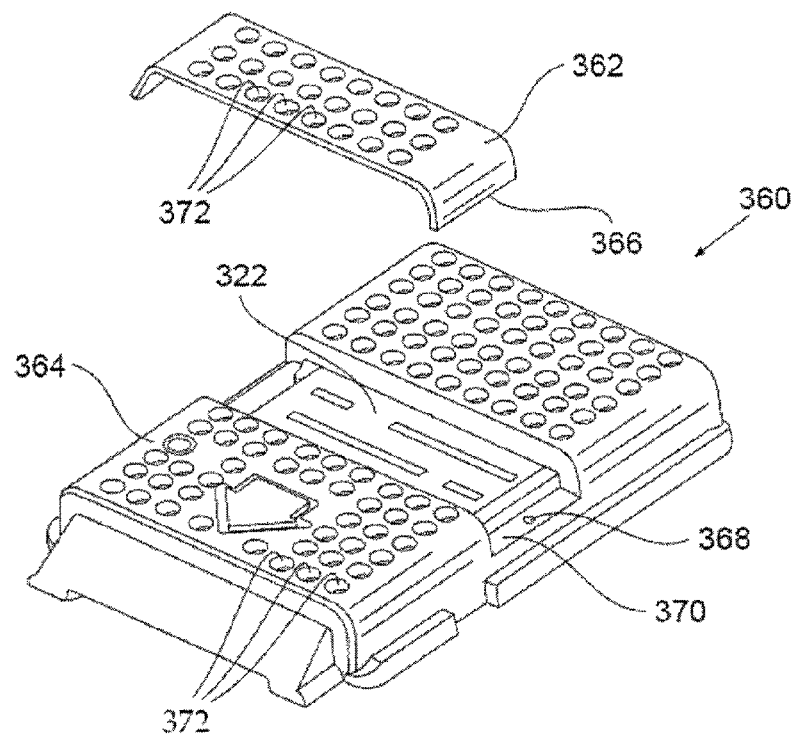
FIG. 14A schematically depicts an embodiment of a cassette usable with the tissue handling device of FIG. 7A and further usable as a sample box, in an exploded view.
Figure 14B:
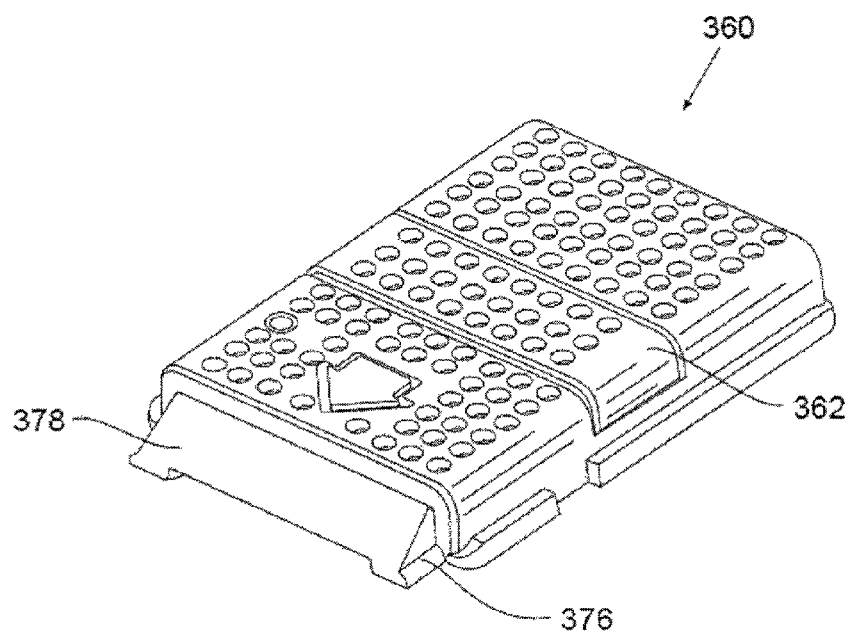
FIG. 14B schematically depicts the cassette of FIG. 14A in a perspective view, from the top.

FIGS. 14A and 14B depict schematically an embodiment of a cassette 360 configured to be used with tissue handling device 200, in a semi exploded view (A) and in a closed state (B). In addition to being usable in conjunction with tissue handling device 200, e.g. according to the description and methods described above, cassette 360 is further usable as a sample box, for holding a sample tissue within during a preparation process prior to sectioning, e.g. washing the sample with a preservative solution, drying the sample, and subsequent steps.

Cassette 360 is different from cassette 260 in having a box cover 362, configured to cover the sample tissue held in the cassette, thereby rendering cassette 360 a closed sample box configured to be used in the sample preparation steps as described above. Box cover 362 has a dimension and shape fitting to window 322 in cassette cover 364. Further, box cover 362 comprises two cover pins 366 for attaching box cover 362 to cassette cover 364. Cassette cover 364 comprises two holes 368 on edges 370 of window 322, substantially fitting in dimensions to cover pins 366. Thus, attaching box cover 362 to cassette cover 364 is achieved by inserting cover pins 366 to holes 368 and pressing onto box cover 362.

Box cover 362 and cassette cover 364 comprise rinsing holes 372, for allowing a washing fluid such as a preservative solution to penetrate easily the cassette and wash the sample tissue. Thus cassette 360 is rendered highly permeable to fluids even when closed by box cover 362.

Cassette base 374 of cassette 360 comprises a labeling surface 378, configured for attaching a label comprising a string for identifying the sample tissue held in the cassette, as well known and is routinely done in the art.

Figures 15A, 15B:
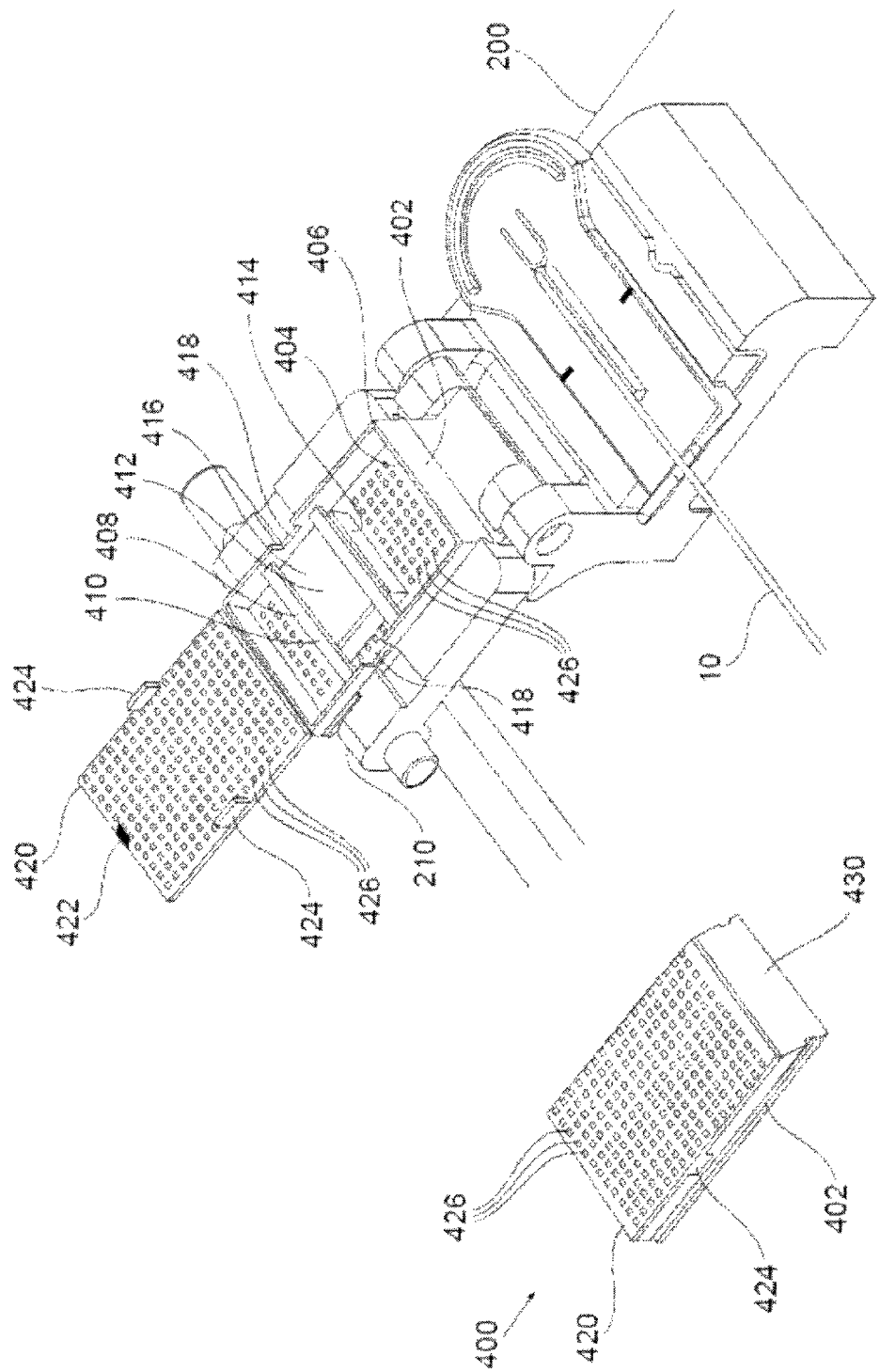
FIG. 15A schematically depicts another embodiment of a cassette usable with the tissue handling device of FIG. 7A and further usable as a sample box, with an open box cover.
FIG. 15B schematically depicts the cassette of FIG. 15A with a closed box cover.

FIGS. 15A and 15B depict schematically yet another embodiment of a cassette 400 configured to be used with tissue handling device 200. Cassette 400 is depicted in FIG. 15A when installed on lever 210 of tissue handling device 200. Cassette 400 may be employed in conjunction with tissue handling device 200 e.g. as is described above, to collect a sample tissue e.g. from a biopsy needle, and may further be employed as a sample box in subsequent steps in the preparation process prior to sectioning.

Cassette 400 comprises a cassette base 402 comprising a compartment 404 confined within base walls 406. A cassette cover 408, comprising a frame 410, is configured to be attached to cassette base 402 inside compartment 404, thereby holding firmly a sample sheet 412 on top of a sponge 414, by pressing the sample sheet and the sponge between the frame and the caste base 402. Frame 410 comprises an open window 416 allowing view and access to sample sheet 412.

Each of the two opposing base walls 406 of cassette base 402 which are perpendicular to the axis of the biopsy needle 10, comprises a depression 418. Depressions 418 are positioned adjacent to the sample sheet and substantially where a biopsy needle, secured in place in tissue handling device 200, touches cassette 400 when lever 210 is moved to a closed potion.

Cassette 400 further comprises a box cover 420, pivotally associated with cassette base 402. Box cover may be open, as is schematically depicted in FIG. 15A, thereby allowing access to sample sheet 412 for attaching e.g. a biopsy sample thereon. By displacing box cover 420 around the pivot and attaching box cover 420 to cassette base 402, box cover 420 may be closed, as is depicted in FIG. 15B. Box cover 420 is attached to cassette base 402 by tongue 422 whereas extensions 424 fit into wall depressions 418 to close them.

Box cover 420 and cassette base 402 further comprise rinsing holes 426, for allowing a washing fluid such as a preservative solution to penetrate easily the cassette and wash the sample tissue. Thus cassette 400 is rendered highly permeable to fluids even when closed by box cover 420.

When a sample tissue adhered to a sample sheet is processed as described above in preparation for section, and particularly during process steps that involve washing, the sample tissue may spontaneously detach from the sample sheet. Moreover, during such process steps the sample tissue may spontaneously tear, and portions of the sample may then detach from the sample sheet. Accordingly, when box cover 420 is closed, (and, likewise, when box cover 362 in cassette 360 is closed), escape of sample tissues from the cassette to the outside is substantially prevented. Furthermore when box cover 420 is closed, (and when box cover 362 in cassette 360 is closed), access to the sample sheet inside the cassette, for attaching a biological tissue thereon, is prevented.

Cassette base 402 of cassette 400 further comprises a labeling surface 430, configured for attaching a label comprising a string for identifying the sample tissue held in the cassette, as well known and is routinely done in the art.

Figure 16A:
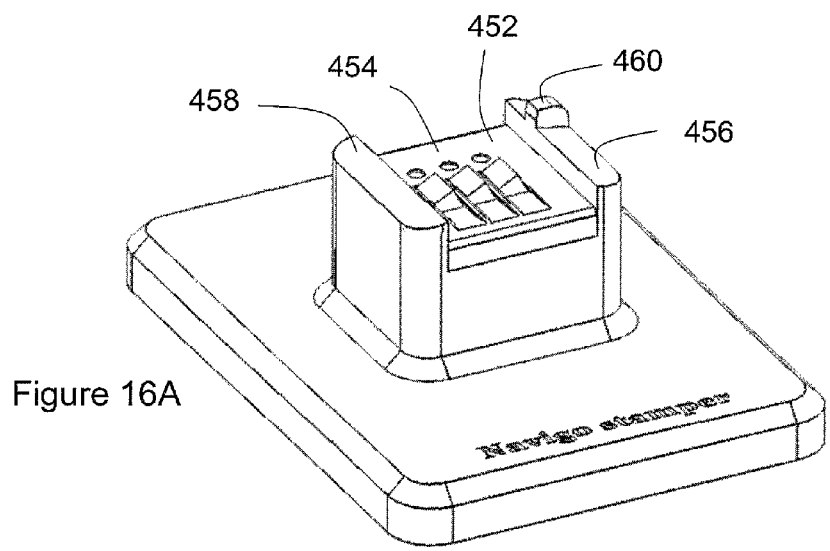
FIG. 16A schematically depicts an embodiment of a dyeing device according to the teachings herein, in perspective view.
Figure 16B:
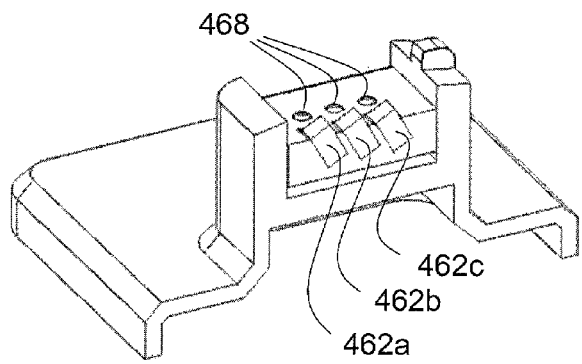
FIG. 16B schematically depicts a cross section of the dyeing device of FIG. 16A, in perspective.
Figure 16C:
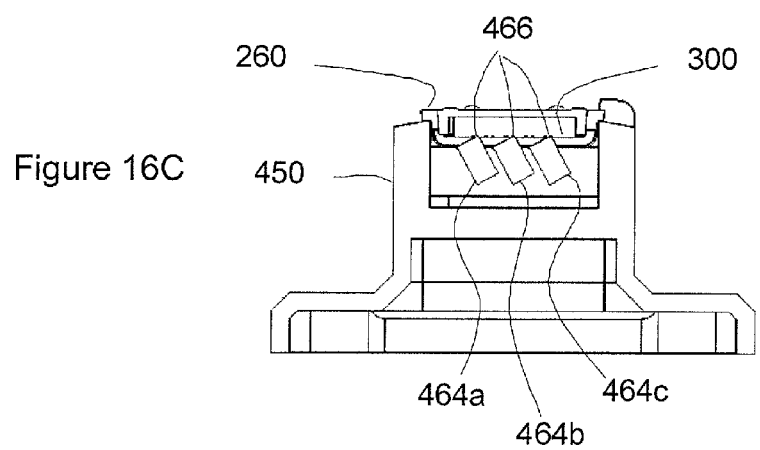
FIG. 16C schematically depicts a cross section of the dyeing device of FIG. 16A with a cassette assembled therein, in side view.

FIGS. 16A-16C schematically depicts a dyeing device 450 for dyeing sample tissues adhered to a sample sheet, e.g. for preserving orientation of the sample tissues during subsequent process steps including inspection under a microscope. Dyeing device 450 comprises a dyeing cassette house 452 configured to house cassette 260. Dyeing cassette house 452 comprises a cassette house floor 454 descended between a first elevated wall 456 and a second elevated wall 458. First elevated wall 456 comprises a protruding tooth 460, arranged to fit to gap 326 in slide 310 of cassette cover 294, thereby allowing to insert cassette 260 to cassette house 452 in a single orientation so that first slide 310 is adjacent first elevated wall 456, and second slide 312 adjacent second elevated wall 458.

Cassette house floor 454 further comprises three dyeing sponges 462a-462c, partially protruding upwards from cassette house floor 454, for dyeing sample sheet 300 in cassette 260 attached thereto, possibly with sample tissues thereon. FIG. 16B schematically depicts a cross-section of dyeing device 450 in a vertical plane comprising dyeing sponges 462a-462c. Dyeing sponges 462a-462c may comprise a permeable and flexible material, capable of sucking liquid spontaneously from a bottom portion to a top portion thereof e.g. by capillarity, thus maintaining the sponges with dye for multiple dyeing sessions. Dyeing device 450 comprises three separated chambers 464a-464c, each configured to contain a dye in a liquid form and a dyeing sponge 462a-462c, respectively. Chambers 464a-464c are substantially rectangular, and arranged tilted diagonally at an angle relative to the vertical, inside cassette house floor 454. Rectangular dyeing sponges 462a-462c that are inserted into chambers 464a-464c are thus consequently tilted, edges 466 forming dying tips, facing upwards towards a sample sheet and a sample tissue to be dyed. In some embodiments sponges 462a-462c are made of regular sponge. Dye can be applied to the sponges e.g. by pouring or dripping dye onto each from above. In some embodiments sponges 462a-462c may be used for multiple dyeing sessions. In some embodiments sponges 462a-462c may be used for a single dyeing event. In some embodiments dyeing device 450 is exposed to body fluids e.g. of marked sample tissue. In some embodiments sponges 462a-462c are disposable. In some embodiments cassette house floor 454 is disposable. In some embodiments dyeing device 450 is disposable.

For use, each dyeing sponge 462a-462c is soaked with a particular dye, for example dyeing sponge 462a may be soaked with a red dye, dyeing sponge 462b may be soaked with a yellow dye and dyeing sponge 462c may be soaked with a blue dye. Three dots 468a-468c, arranged on cassette house floor 454 adjacent dyeing sponges 462a-462c, respectively, are colored each by the dye used with the respective dyeing sponge, for informing a user what color each dyeing sponge may mark a sample tissue with. Dye materials used for soaking sponges 462a-462c and consequently for marking sample tissues are such that endure subsequent process steps of the sample tissue and remain adhered to the sample tissue, such as TMD™ Tissue Marking Dyes by Triangle Biomedical Sciences or such as Tissue Marking Dyes® (for example model numbers 0728-x) by Cancer Diagnostics, Inc., or any other suitable dye as is known in the art.

In use, cassette 260 is suitably placed inside dyeing cassette house 452 aligned as described above and with a sample sheet 300 including at least one sample tissue facing downwards towards cassette house floor 454. It is noted that a sample tissue attached to sample sheet 300 is generally aligned having its long dimension crossing all three dyeing sponges. FIG. 16C schematically depicts a cross section, along a vertical plane as in FIG. 16B, of dyeing device 450, having a cassette 260 suitably assembled in dyeing cassette house 452. It is noted that in FIG. 16C, a sample tissue attached to sample sheet 300 is generally aligned having its long axis parallel to the plane of the Figure. Edges 466 are substantially at a height above cassette house floor 454 that ensures contact of edges 466 with sample sheet 300, and consequently with sample tissues attached thereto. A sample tissue attached to sample sheet 300 typically protrudes from sample sheet 300 downwards towards dyeing sponges 462a-462c, thereby sinking slightly into the sponges when pressed towards the sponges. Sponges 462a-462c thus yield to the pressure of the sample tissue, thereby marking the sample tissue along a substantial portion of the tissues' cross-section perimeter. Marking the sample tissue around the perimeter of the sample tissue and at least around a substantial portion thereof allows for colored markings on sequential slices of the sample tissue rather than only on the first slice.

Figure 17:
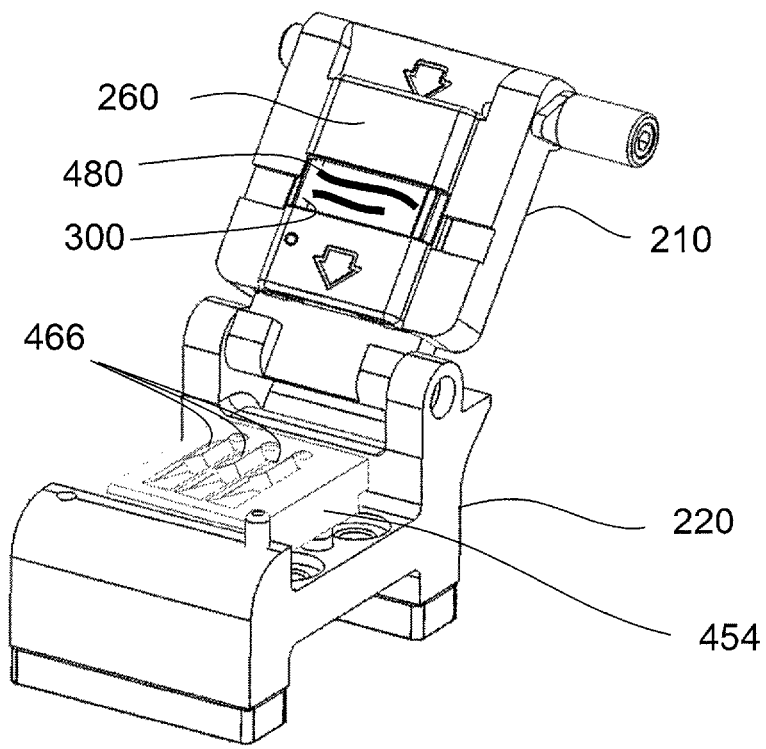
FIG. 17 schematically depicts an embodiment of a lever comprising a cassette with a sample sheet, and an embodiment of a cassette house floor configured for dyeing, assembled onto the pedestal of the tissue handling device of FIG. 7A.

According to an aspect of some embodiments, a dyeing device comprising a cassette house floor such as cassette house floor 454 of dyeing device 450, may be configured to be attached, permanently or temporarily, to a base such as base 202 of tissue handling device 200. According to some such embodiments, a cassette house floor such as cassette house floor 454 may comprise two pins extending downwards from a bottom surface thereof and arranged to fit into through holes 236 in pedestal 220. According to some such embodiments, needle bed 208 and needle bed holder 222 may be disassembled from pedestal 220 by lifting upwards, e.g. by hand. A cassette house floor, comprising two pins extending downwards as described above and further comprising dyeing sponges on a top surface thereof such as in cassette house floor 454, may then be attached onto pedestal 220 instead of needle bed holder 222, as is schematically depicted in FIG. 17. It is noted that a replacement of needle bed holder 222 with a cassette house floor for dyeing a sample tissue as described above may thus be accomplished easily and quickly, by hand.

According to an aspect of some embodiments a method of dyeing a sample sheet, possibly carrying one or more sample tissues thereon, and using a tissue handling device such as tissue handling device 200 is thus provided. Cassette 260 comprising sample sheet 300 is assembled to lever 210, and a biopsy gun comprising a biopsy sample tissue in the notch thereof is positioned in gun house 204. The biopsy needle is suitably arranged on needle bed 208 and the sample tissue is collected to cassette 260, by lowering lever 210 to a closed position as described and explained above. After collecting the sample tissue onto sample sheet 300 in cassette 260 and lifting lever 210 to an open position, the biopsy gun is removed from gun house 204. Needle bed holder 222 together with needle bed 208 thereon are disassembled from pedestal 220, and a cassette house floor comprising pins for attachment to pedestal 220 and fitting to through holes 236 therein is attached to pedestal 220 as explained above. Lever 210, comprising cassette 260 with a sample tissue 480 adhered thereto, is lowered again to a closed position bringing sample sheet 300 and the sample tissue thereon substantially into contact with the sponges on the cassette house floor on pedestal 220. Then lever 210 is lifted, sample sheet 300 and the sample tissue in cassette 260 being marked.

The method described above is particularly advantageous because the two steps of collecting a sample tissue onto the sample sheet and marking the sample sheet are employed using a single device. Consequently, disassembling the cassette from a first device and then assembling the cassette in a second device between the two steps is avoided, leading to a substantial reduction in risk to the cassette and the samples thereon. Further, a higher accuracy associated with the location of the marks on the sample sheet may be attained, because substantially fewer mechanical tolerances are accumulated in carrying out the method.

Figure 18:
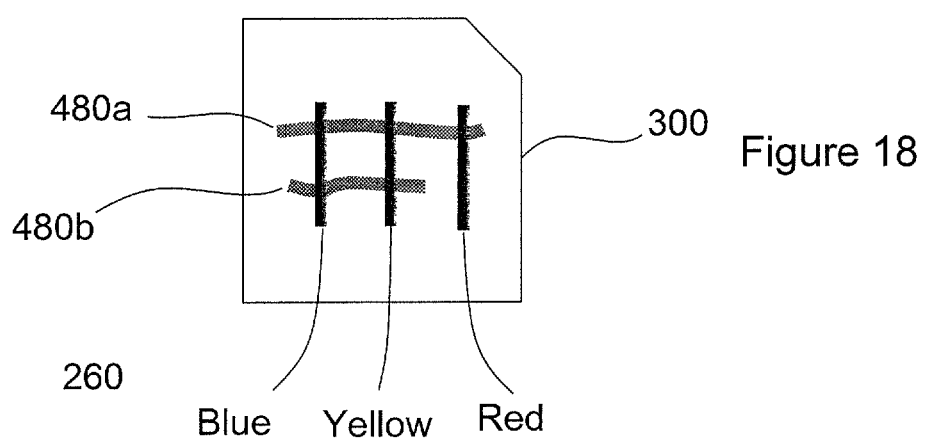
FIG. 18 schematically depicts an embodiment of a sample sheet with sample tissues adhered thereon and dyed according to the teachings herein.

FIG. 18 schematically depicts an exemplary sample sheet 300 with a long sample tissues 480a and short sample tissue 480b, following coloring using e.g. dyeing device 450 as described above. The truncated corner of sample sheet identifies the orientation of the sample tissues relative to the biopsy needle and the distal tip as described above. Consequently, employing the example provided above of the order of the three dyes in dyeing device 450, the end of the sample tissues closer to the truncated corner is colored red, the other end is colored blue and the middle is yellow.

By coloring sample tissues with a mark as described above, and possibly with more than one mark as described above, information of original orientation and location of the sample tissue is preserved as is detailed below:
  The location of the notch of the biopsy needle—and the location of the notch ends—relative to sample sheet 300, when a sample tissue is attached to sample sheet 300 using tissue handling device 200, is dictated by handling device 200 and is known, as described above;
  The location of the marks marked by dyeing device 450 on sample sheet 300 are dictated by dyeing device 450, and known, as described above;
  Consequently, the marks identify on the sample tissues locations that can be traced back, namely can be correlated, to the notch (or any other particular point) on the biopsy needle.
  When, during processing a sample tissue prior to inspection, the sample tissue or a portion thereof is removed from the sample sheet—e.g. slices of the sample tissue are taken for inspection under a microscope—the marks still identify on the sample portion both orientation and location of that portion relative to the biopsy needle notch.
  It is noted that by using several marks side by side as is described above, and preferably by using several marks with different colors, such orientation and location information is retained also on short or partial sample tissues such as short sample tissue 170b: if a short sample tissue is marked with only two marks (of different colors), full information of orientation and location is maintained on the sample tissue; if a very short sample tissue is marked with only a single mark, the original location of very short sample tissue is still known (although orientation information might be lost).

According to an aspect of some embodiments of the invention, there is provided a method for handling biological tissues obtained with a core biopsy needle.

1. When lever 210 is lifted (namely, being in an open position), an assembled cassette 260 comprising a sample sheet 300 is attached to lever 210. A first position of the cassette is selected for attaching a sample tissue on the sample sheet;

2. A biopsy gun 78 carrying a sample tissue in the exposed notch 18 of the needle 10 (the cannula is pulled back) is placed and secured in gun house 204 of tissue handling device 200, so that the needle is between alignment shoulders 240 and supported by support platform 244 of needle bed 208;

3. Lever 210 is lowered until it is stopped by stopper pillar 238, thereby pressing sample sheet 300 in cassette 260 onto the sample tissue on the needle and attaching the sample tissue to the sample sheet;

4. Lever 210 is lifted and cassette 260 is optionally moved to a next position for attaching a next sample tissue on the same sample sheet, according to steps 1-3;

5. Cassette 260 is disassembled from lever 210, and inserted to dyeing device 450 for marking the sample tissues.

6. Cassette 260 is disassembled and the sample sheet 300 carrying marked sample tissues on it is removed from the cassette;

7. Sample sheet 300 carrying sample tissues 480 is placed in sample box 500, as is illustrated in FIG. 19A. The sample box is closed with sample box cover 502, and the closed sample box with the sample tissues on the sample sheet inside is taken through a suitable chemical preparation process prior to examination, as is described in the introduction above. In some embodiments cassette 260 may not be disassembled in step 6 above but may rather be inserted, assembled, to preservative solution such as a solution including formaldehyde. Subsequently cassette 260 is disassembled and the sample sheet is placed inside a sample box 500 as described above for the subsequent steps of the chemical processing;

8. After the chemical preparation process, the dried sample sheet with sample tissues thereon is removed from the sample box and placed face down on the floor of a metal mold 510, so that the sample tissues touch directly the floor of the metal mold, as is illustrated in FIG. 19B. The sample tissues may be adhered to the floor of the metal mold 510 by slight pressing, and optionally using a drop of paraffin;

9. Sample box 500 is fixed on top of metal mold 510, as is illustrated in FIG. 19C, and the space within, that is to say between the metal mold and the sample box, is filled with paraffin;

10. After the paraffin solidifies the metal mold is removed, leaving the sample box (with the marked string 512 identifying the sample tissues) filled with a block of paraffin 514 and with the sample tissue still adhered to the sample sheet, on top, as is schematically illustrated in FIG. 19D;

11. The sample box with the sample tissue is taken for slicing, as is explained above;

12. A selected slice is placed on a first glass plate and is heated and then cleaned with designated detergents to expel the paraffin. A second glass plate is then attached on top of the sample tissue, so that the sample tissue is between the first and second glass plates, and the sample tissue between two glass plates is taken for examination, e.g. under a microscope;

13. A region of interest on the inspected sample tissue, for example a tumor or a diseased portion, can be localized relative to the marks on the sample tissue, and consequently can be localized relative to the biopsy needle notch and, if desired, to the location in the organ from where it was taken.

It is noted that when cassette 360 or cassette 400 is used rather than cassette 260, the steps of disassembling the cassette (in step 6 above), removing the sample sheet from the cassette and placing the sample sheet in a sample box as is illustrated in FIG. 19A become redundant. Thus, when a cassette such as cassette 360 or cassette 400 is used, the following steps may be employed following dyeing the sample tissue in step 5 above:

6a. A box cover such as box cover 362 in cassette 360 or box cover 420 in cassette 400 is attached to the cassette thereby closing the window of the cassette.

7a. The closed cassette with the sample tissues on the sample sheet inside is taken through a suitable chemical preparation process prior to examination, as is described in step 7 above.

The next steps are substantially similar to the steps 8-13 above. For example, following step 7a, the box cover is removed and the cassette (such as 360 or 400) is disassembled, the sample sheet is removed and placed, face down, in a metal mold as described in step 8 above and illustrated in FIG. 19B. Subsequently, the cassette, rather than a sample box, is placed on top of the metal mold, and labeling surface such as labeling surface 378 in cassette 360 is used for labeling the resulting paraffin block with the sample tissue therein. Thus, by employing a cassette such as cassette 360 or cassette 400, direct handling with the sample sheet with the sample tissues adhered thereon is minimized, thereby reducing risk of damage to sample tissue or loss of sample tissues, and further reducing the complexity of the process and hence reduces the time of the process.

Figure 20:
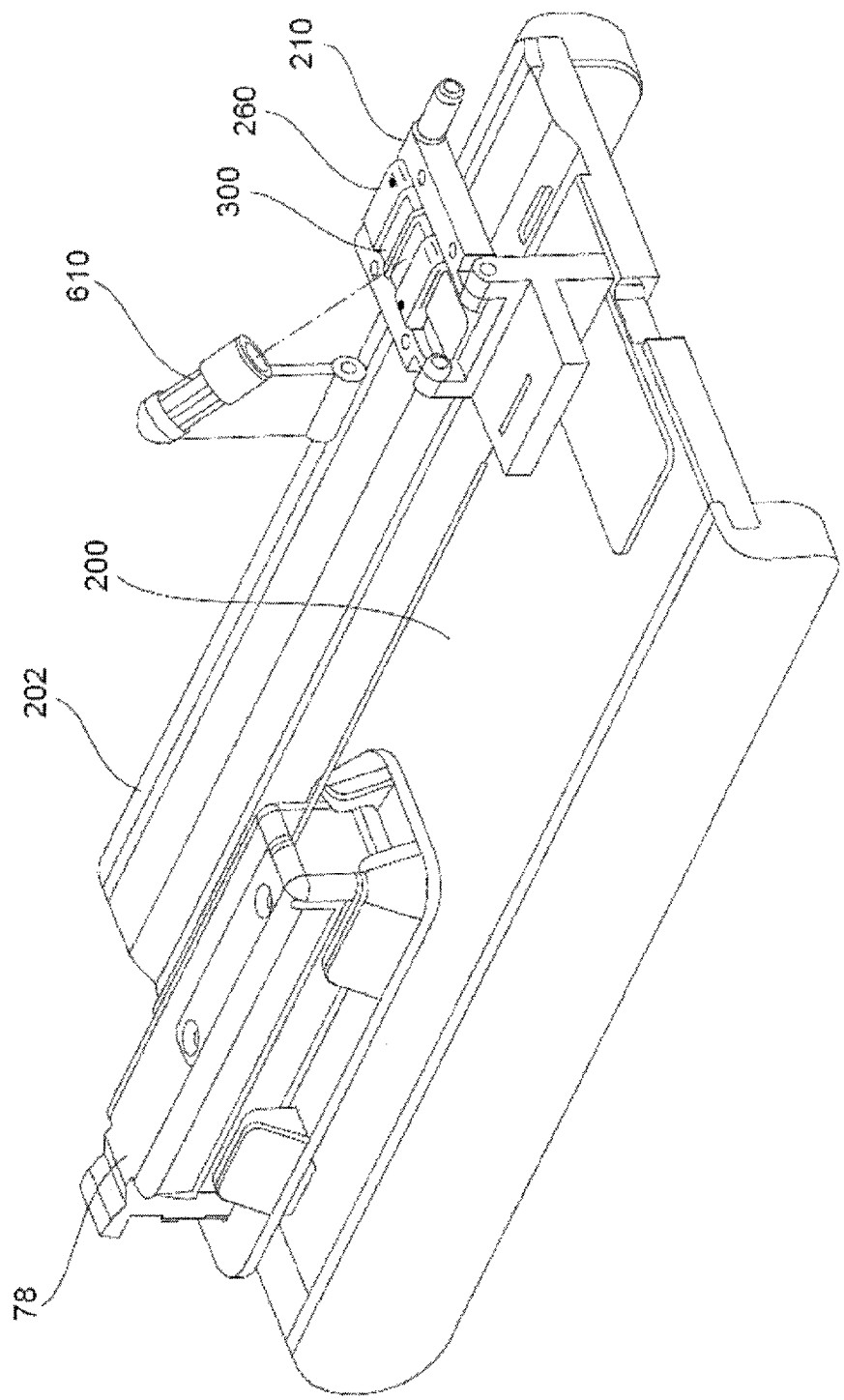
FIG. 20 schematically depicts a tissue handling device comprising the tissue handling device of FIG. 7A and further comprising a CCD camera configured to obtain images of the sample sheet when the lever is in an open position.

According to some embodiments, an image of the sample tissue on the sample sheet is taken, immediately after collecting the sample tissue from the notch, using an imaging modality such as a camera. FIG. 20 schematically depicts tissue handling device 600 comprising tissue handling device 200 and further comprising a camera 610 fixedly installed on base 202 and configured to obtain an image of sample sheet 300 in cassette 260, when lever 210 is in an open position as is depicted in FIG. 20.

Camera 610 is employed to obtain an image of the location of the sample tissue relative to the sample sheet and particularly relative to a mark on the sample sheet such as truncated corner 328 or relative to an edge of the sample sheet.

To maintain knowledge of sample orientation, the sample itself must be marked, e.g. a colored dot may be marked on the sample tissue. The sample tissue may be marked at any arbitrary location on the sample if marking is done prior to obtaining an image using camera 610. Alternatively the sample should be marked at a known point such as the end of the sample closest to the distal tip of the needle, thereby identifying that end of the sample. Following slicing of the sample and during an inspection under a microscope, the pathologist may indicate e.g. a tumor at a distance from the marked dot on the sample tissue. The location of the marked dot on the sample is known from the image taken by camera 610 (either the dot appears in the image or the location of the dot is the location of the end the sample, which always appears in the image). Hence, the exact location of the tumor may be traced back to a particular location along the biopsy needle at the moment the biopsy sample was taken.

By recording the position of the distal tip of the needle inside the live organ while taking the sample tissue, for example by using techniques as is explained in the introduction above, the position of the distal tip of the needle at the moment of taking the sample tissue is known. By measuring, using the marks on the sample tissue, the distance between an end of the sample tissue and the needle distal tip, or between an end of the sample tissue and an end of the sample sheet, the position of any point on the sample tissue relative to the distal tip is known. By preserving tissue orientation until examination, any disease or tumor detected in examination is correlated to an identified end of the sample tissue. By considering the above mentioned pieces of information, a tumor or disease detected in examination can be correlated to an identified location inside the live organ from which the sample tissue was taken.

Herein are provided devices and methods that in some aspects improve techniques for handling biological tissues that are taken with a biopsy needle. Specifically, devices and methods are provided herein that in some embodiments maintain sample tissue orientation and/or allow Z axis accuracy of not more than 1 millimeter and even Z axis accuracy better than 1 millimeter.

Devices and methods are provided that in some embodiments enable increased disease detection probability. Straight sample tissues on the sample sheet enable increased disease detection probability.

Thus, according to an aspect of some embodiment, there is provided a device for collecting onto a sample holder a biological tissue carried on a shaft. The device comprises a base, a lever and a needle bed. The needle bed is attached to one of the base and the lever and is configured to support, substantially in a pre-defined position, a shaft carrying a biological tissue. The other one of the base and the lever is configured to support a sample holder attached thereto. The lever is movable between settings relative to the base, thereby a sample holder suitably attached to the device is movable relative to the needle bed, so that:

in a first setting the sample holder and the needle bed are distant from one another, and in a second setting the sample holder and the needle bed are situated proximal to one another having a predefined arrangement relative to one another.

According to some embodiments the needle bed is attached to the base and the lever is configured to be attached to a sample holder. According to some embodiments the needle bed is attached to the lever and the base is configured to be attached to a sample holder.

According to some embodiments the lever is detachable from the base. According to some embodiments the lever is not detachable from the base.

According to some embodiments the lever is pivotally associated with the base thereby being movable between the settings relative to the base substantially along a curve. According to some embodiments the lever is mechanically associated with the base by a track, thereby being movable between the settings relative to the base substantially along the track. According to some embodiments the track comprises one or more rails. According to some embodiments the track comprises one or more grooves.

According to some embodiments the needle bed is detachable from the device.

According to some embodiments the needle bed is a disposable part.

According to some embodiments the sample holder and the needle bed face one another in the second setting.

According to some embodiments the sample holder may contact a biological tissue carried by a shaft supported by the needle bed when the lever is in the second setting.

According to some embodiments the shaft is a core biopsy needle. According to some embodiments the shaft is a core biopsy needle having a notch. According to some embodiments the notch of the core biopsy needle comprises a notch floor configured to carry a biological tissue.

According to some embodiments the needle bed is configured to support a core biopsy needle so that the notch floor is substantially parallel to the sample holder when the lever is in the second setting. According to some embodiments a biological tissue carried on the notch is pressed between the sample holder and the notch floor when the lever is in the second setting.

According to some embodiments the needle bed is configured to support a core biopsy needle so that the notch floor is not parallel to the sample holder when the lever is in the second setting. According to some embodiments the needle bed is configured to support a core biopsy needle so that the notch floor is perpendicular to the sample holder when the lever is in the second setting. According to some embodiments a biological tissue carried on the notch is not pressed between the sample holder and the notch floor when the lever is in the second setting.

According to some embodiments the tissue collecting device further comprises a gun house configured to secure to the device a biopsy gun having a biopsy needle so that the biopsy needle is supported by the needle bed in the pre-defined position.

According to some embodiments the gun house has an adjustable dimension and/or shape. According to some embodiments the gun house has fixed dimensions and shape.

According to some embodiments the sample holder is capable of adhering to a biological tissue by contacting the biological tissue. According to some embodiments the sample holder is configured to contact, in the second setting, a biological tissue carried on the shaft, thereby adhering to the biological tissue and detaching the biological tissue from the shaft when the lever is moved to the first setting.

According to some embodiments the sample holder is configured to hold a sample sheet capable of adhering to a biological tissue by contacting the biological tissue. According to some embodiments the sample holder comprises a sample sheet, capable of adhering to a biological tissue by contacting the biological tissue.

According to some embodiments the sample holder comprises a cassette configured to hold a biological tissue collected from a shaft by the device. According to some embodiments the cassette is detachable from the device by hand. According to some embodiments the cassette is configured to hold a sample sheet, capable of adhering to a biological tissue by contacting the biological tissue. According to some embodiments the sample sheet is configured to contact, in the second setting, a biological tissue carried on the shaft, thereby adhering to the biological tissue and detaching the biological tissue from the shaft when the lever is moved to the first setting. According to some embodiments the cassette has an unsymmetrical external outline precluding rotational symmetry of the cassette, except for the trivial rotational symmetry of 360 degrees. According to some embodiments the cassette may be attached to the device only in a single orientation of the cassette relative to the base of the device. According to some embodiments a biological tissue is attached to the sample holder so that an orientation of the biological tissue on the notch is substantially maintained on the sample holder.

According to some embodiments the sample holder is controllably displaceable relative to the device when attached to the device. According to some embodiments the sample holder is controllably displaceable between several well-defined positions, thereby allowing collecting sequentially onto several locations on the sample holder, several biological tissues, respectively.

According to some embodiments the needle bed is flexibly attached to the device thereby being able to tilt relative to the device and align substantially parallel to the sample holder when the lever is in the second setting. According to some embodiments the needle bed is flexibly attached to the device thereby being able to yield relative to the device when the lever is in the second setting.

According to some embodiments the tissue collecting device further comprises an imaging modality fixedly attached to the base and aimed and configured to obtain an image of the sample holder when the lever is in the first setting. According to some embodiments the imaging modality is a CCD camera.

According to an aspect of some embodiment, there is provided a cassette for collecting and holding a biological tissue on a sample holder, comprising: a cassette base comprising a base slab, and a cassette cover comprising a window and disposed, in an assembled cassette, above the cassette base. The cassette is configured to be assembled with a sample holder having an adhering surface configured to adhere to a biological tissue, the sample holder being held substantially between the cassette base and the cassette cover whereas at least a portion of the adhering surface is accessible through the window.

According to some embodiments the sample holder comprises a sample sheet. According to some embodiments the cassette further comprises the sample holder, disposed substantially between the cassette base and the cassette cover. According to some embodiments the sample holder is capable of adhering to a biological tissue by contacting the biological tissue on the adhering surface.

According to some embodiments the cassette has an unsymmetrical external outline precluding rotational symmetry of the cassette, except for the trivial rotational symmetry of 360 degrees. According to some embodiments the sample holder is held by being pressed along a portion thereof between the cassette base and the cassette cover. According to some embodiments the sample holder comprises a mark, the mark precludes rotational symmetry of the sample holder except for the trivial rotational symmetry of 360 degrees. According to some embodiments the mark is a visual mark. According to some embodiments the mark is a structural. According to some embodiments the mark is a hole in a the sample holder. According to some embodiments the hole is a through-hole. According to some embodiments the adhering surface has a substantially rectangular shape and the mark is a truncated corner of the rectangle.

According to some embodiments the cassette is configured to hold the sample holder in a single orientation by comprising an internal structure compatible with the structural mark of the sample holder. According to some embodiments the internal structure comprises a pillar. According to some embodiments the internal structure comprises a protrusion. According to some embodiments the internal structure comprises an unsymmetrical compartment. According to some embodiments the compartment has a substantially rectangular shape with a truncated corner.

According to some embodiments the cassette further comprises a flexible layer disposed between the cassette base and the cassette cover so that a sample sheet is held in the assembled cassette between the flexible layer and the cassette cover. According to some embodiments the flexible layer comprises a sponge.

According to some embodiments the cassette further comprises a box cover configured to cover the window. According to some embodiments the box cover covers the window by attaching to the cassette base or to the cassette cover. According to some embodiments the box cover comprises through holes for rendering the cassette permeable to fluid. According to some embodiments the cassette further comprises a labeling surface configured for attaching thereon a label comprising an identification string.

According to an aspect of some embodiment, there is provided a dyeing device configured for dyeing a biological tissue adhered to a sample holder having a pre-defined external outline. The dyeing device comprises: a sample holder house having a shape compatible with the pre-defined external outline of the sample holder, thereby being configured to house the sample holder, and a protruding dyeing tip positioned in the sample holder house and configured to dye a biological tissue upon contacting the biological tissue. The protruding dyeing tip is configured to contact a biological tissue carried on a sample holder that is suitably positioned in the sample holder house, thereby dyeing the biological tissue.

According to some embodiments the sample holder comprises a cassette as described above.

According to some embodiments the dyeing device comprises at least two dyeing tips, wherein each dyeing tip is configured to dye a biological tissue with a different colour, respectively.

According to some embodiments the tissue handling device described above further comprises a dyeing module comprising a dyeing tip configured for selectively colouring a biological tissue in a portion thereof by contacting the portion with the dyeing tip. According to some embodiments a sample holder is attached to the lever and wherein in a setting of the lever relative to the base the sample holder may contact the dyeing module so that a biological tissue attached to the sample holder is selectively coloured in a portion thereof.

According to an aspect of some embodiment, there is provided a device for dyeing a biological tissue carried on a sample holder. The device comprises a base, a lever and a dyeing module comprising a dyeing tip. The dyeing module is attached to one of the base and the lever. The other of the base and the lever is configured to support a sample holder attached thereto. The lever is movable between settings relative to the base, thereby a sample holder attached to the device is movable relative to the dyeing module, so that in a first setting the sample holder and the dyeing module are distant from one another. In a second setting the sample holder and the dyeing module are situated proximal to one another having a predefined arrangement relative to one another.

According to some embodiments the dyeing module is attached to the base and the lever is configured to be attached to a sample holder. According to some embodiments the dyeing module is attached to the lever and the base is configured to be attached to a sample holder. According to some embodiments the dyeing tip contacts the sample holder when the lever is in the second setting. According to some embodiments the dyeing tip contacts a biological sample adhered to the sample holder when the lever is in the second setting.

Methods described herein facilitate maintaining order while handling sample tissues, thus minimizing mistakes as to patient's biopsy misplacement. Since the sample tissues are handled with the sample sheet through most steps in the preparation to examination process, from harvesting to the mold, misplacement of sample tissues and likelihood of errors is lowered.

The method described herein considerably reduces labor in handling sample tissues. Further, the method described herein minimizes damage to sample tissues and loss of sample tissues portions. As sample tissues are handled while adhered to a sample sheet.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention is described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A cassette for collecting and holding a biological tissue on a sample sheet, comprising:
   a cassette base comprising a base slab,
   a cassette cover comprising a window and configured to be releasably attached to said cassette base above said cassette base, and
   a sample sheet having an adhering surface and disposed, in an assembled cassette, substantially between said cassette base and said cassette cover, so that at least a portion of said adhering surface is accessible through said window for receiving a biological tissue thereon, said adhering surface being configured to adhere to a biological tissue upon contacting or pressing a biological tissue initially carried on a metal shaft, so as to enable detaching said biological tissue from said metal shaft by distancing said cassette from said metal shaft, so that said biological tissue remains stuck on said adhering surface, said sample sheet further comprising a structural mark precluding rotational symmetry of said sample sheet except for a trivial rotational symmetry of 360 degrees,
   wherein said cassette further comprises an unsymmetrical compartment for said sample sheet, compatible with said structural mark, thereby being configured to hold said sample sheet in a single orientation.

2. The cassette of claim 1 having an unsymmetrical external outline precluding rotational symmetry of said cassette, except for a trivial rotational symmetry of 360 degrees.

3. The cassette of claim 2, wherein said base further comprises at least one flexible member disposed on an outer surface of said cassette, and configured, when said cassette is installed in a tissue handling device, to flexibly stabilize said cassette when a biological tissue is collected on said sample sheet.

4. The cassette of claim 1, wherein said metal shaft comprises a core biopsy needle having a notch and wherein said window comprises at least two window edges aligned lower than said adhering surface when said adhering surface faces upwards, so that when said core biopsy needle is arranged above said adhering surface with said notch facing said adhering surface and arranged between two said window edges and said core biopsy needle is pressed downwards towards said adhering surface, said adhering surface inserts into said notch.

5. The cassette of claim 1, further comprising a flexible layer disposed between said cassette base and said cassette cover and configured to support said sample sheet in said assembled cassette between said flexible layer and said cassette cover.

6. The cassette of claim 5, wherein said flexible layer comprises a sponge.

7. The cassette of claim 1, further comprising a box cover configured to cover said window.

* * * * *